(12) United States Patent
Picoul et al.

(10) Patent No.: US 7,816,520 B2
(45) Date of Patent: Oct. 19, 2010

(54) 5,6-DIPHENYL-1,2,4-TRIAZINIC DIMERIC DERIVATIVES AND THE USE THEREOF IN THE FORM OF SUN-PROTECTIVE AGENTS

(75) Inventors: Willy Picoul, Lyons (FR); Marco Ciufolini, Vancouver (CA); Pascal Bordat, Mervilla (FR); Roger Tarroux, Toulouse (FR)

(73) Assignees: Pierre Fabre Dermo-Cosmetique, Boulogne-Billancourt (FR); Centre National de la Recherche Scientifique (CNRS), Paris (FR); Universite Claude Bernard Lyon 1, Villeurbanne (FR)

( * ) Notice: Subject to any disclaimer, the term of this patent is extended or adjusted under 35 U.S.C. 154(b) by 550 days.

(21) Appl. No.: 11/579,538

(22) PCT Filed: May 4, 2005

(86) PCT No.: PCT/FR2005/001132
§ 371 (c)(1),
(2), (4) Date: Jan. 17, 2008

(87) PCT Pub. No.: WO2005/121128
PCT Pub. Date: Dec. 22, 2005

(65) Prior Publication Data
US 2008/0267892 A1    Oct. 30, 2008

(30) Foreign Application Priority Data
May 5, 2004    (FR) .................................. 04 04811

(51) Int. Cl.
C07D 403/10 (2006.01)
C07D 403/12 (2006.01)
C07D 403/14 (2006.01)
A61K 8/49 (2006.01)
A61Q 17/04 (2006.01)

(52) U.S. Cl. .................. 544/182; 252/301.23; 424/70.9
(58) Field of Classification Search ................. 544/182; 252/301.23; 424/70.9
See application file for complete search history.

(56) References Cited

U.S. PATENT DOCUMENTS

| 3,211,729 A | 10/1965 | Siegrist et al. |
| 5,202,471 A | 4/1993 | Chandraratna |
| 6,193,960 B1 | 2/2001 | Metzger et al. |

FOREIGN PATENT DOCUMENTS

| DE | 247 899 A1 | 7/1987 |
| EP | 0 818 950 A1 | 1/1998 |
| FR | 2 803 194 | 7/2001 |

OTHER PUBLICATIONS

Pitet et al., Boll. Chim. Farm., vol. 119, pp. 469-482 (1980).
Fengeai et al., Gaofenzi Tongxun, vol. 5, pp. 319-324 (1981).
Yi et al., Journal of Applied Polymer Science, vol. 82, pp. 907-915 (2001).
Case, Heterocycl. Chem, vol. 8, pp. 1043-1046 (Dec. 1971).
Wahl et al., Die Makromolekulare Chemie, vol. 176, pp. 849-858 (1975).

Primary Examiner—Venkataraman Balasubramanian
(74) Attorney, Agent, or Firm—Birch, Stewart, Kolasch & Birch, LLP.

(57) ABSTRACT

The invention relates to 5,6-diphenyl-1,2,4-triazinic compounds of general formula (I), wherein identical or different R1, R2, R3 and R4 represent a hydrogen, fluoride, chloride or bromine atom, C1 to C12 linear or branched alkyl, C1 A C18 linear or branched hydroxy, alkoxy poly(ethoxy)-alkoxy with a C1 to C4 alkyl fragment and an ethoxy number ranging from 1 to 4, amino or mono or di-alkylamino with a C1 to C4 alkyl fragment group, X is ortho-, meta- or paraphenylene, 4,4'-biphenylene, 2,4- or 2,6- or 3,4- or 3,5-pyridinylene, 2,2'-bipyridinylene, meta- or paraphenylenediamino, ethylenediamine, 2,2'-piperazinylene, diacyl of formula -(R4CO)2-, wherein r represents a phenyl radical, a 3 to 10 carbon, phenanthrene or anthracene atoms alkyl chain except 1,4-bis (5,6-diphenyl-1,2,4-triazin-3-yl)benzene of 2,4-bis(5,6-diphenyl-1,2,4-triazin-3-yl)pyridine and of 2,6-bis(5,6-diphenyl-1,2,4-triazin-3-yl)pyridine, to cosmetic compositions containing said compounds and to the use thereof in the form of sun filters or light-protective agents.

12 Claims, 2 Drawing Sheets

5,6-DIPHENYL-1,2,4-TRIAZINIC DIMERIC DERIVATIVES AND THE USE THEREOF IN THE FORM OF SUN-PROTECTIVE AGENTS

The present invention relates to 5,6-diphenyl-1,2,4-triazine derivatives, and in particular to the use thereof as sun filters on human skin and hair or as light-protective agents in the synthetic materials industry such as plastics, glass and textiles. The present invention also has as an object cosmetic compositions containing the aforesaid derivatives.

As a brief review, the action of solar radiation on the skin depends primarily on the energy of the radiation which reaches the various cutaneous layers. Generally speaking, the most energetic radiation, i.e., having the shortest wavelength ($E=hc/\lambda$), cause erythemas or "sunburn", whereas less energetic radiation only causes a simple browning of the skin. It is thus considered that a sun filter intended to be part of the composition of so-called "sunscreen" cosmetic preparations must absorb short wavelength radiation to the maximum degree possible while remaining transparent to radiation of longer wavelength.

Photobiologists typically divide the ultraviolet spectrum into three parts, called UV-A, UV-B and UV-C, which correspond to the decreasing wavelength ranges from 400 nm to 320 nm, from 320 nm to 280 nm and from 280 nm to 200 nm, respectively.

UV-B and UV-A allow the tanning of the human epidermis. UV-B causes erythemas and cutaneous burns which can harm the development of a natural tan. For these reasons, as well as for esthetic reasons, a constant demand exists for methods of controlling this natural tanning with a view to controlling the color of the skin. It is thus advisable to filter this UV-B radiation.

It is also known that UV-A rays are likely to induce a deterioration of the skin, in particular in the case of sensitive skin or skin continuously exposed to sun radiation. In particular, UV-A rays cause a loss of skin elasticity and the appearance of wrinkles which lead to premature aging. They cause the triggering of the erythematous reaction or amplify this reaction in certain subjects and can even be the cause of phototoxic or photoallergic reactions. It is thus desirable to UV filter-A radiation as well.

UV-C, which is the most highly energetic, causes photokeratitis. The ozone formed in the stratosphere generally absorbs a large part of this UV-C radiation which, on the other hand, is found in large amounts in the radiation emitted by artificial lamps, which are often responsible for serious cutaneous injuries. UV-B, which penetrates the skin layer and, in particular, the stratum mucosum of the epidermis, causes solar erythemas. Consequently, UV-B and UV-C radiation together constitute the so-called erythema spectrum with regard to which sun filters must act as a screen. UV-A produces the direct pigmentation of the skin (melanogenesis), i.e., the tanning of the skin.

Compounds derived from the benzotriazoles and/or the benzotriazoles are known as UV filters, in particular in the field of cosmetics. The patent application FR 2,803,194 thus disclosed S-triazine derivatives carrying phenylbenzothiazole or benzothiazole groups useful as UV filters in particulate form. These compounds cover the range of UV-A and of UV-B but they exhibit the major disadvantage of absorbing in the visible spectrum (wavelengths longer than 400 nm). Thus these products are heavily colored, which limits their use in cosmetic products.

The present invention proposes novel 5,6-diphenyl-1,2,4-triazine derivatives capable of absorbing in UV-A and/or UV-B and/or UV-C, without absorbing in the visible spectrum. Thus these compounds have the advantage of being lightly colored.

They also have the advantage of being capable of being specific to one of these spectra. This is advantageous when it is desired to filter a specific UV spectra (UV-A, UV-B or UV-C), for example to supplement the spectral effectiveness of a UV filter which exhibits a gap in this specific range.

These novel derivatives thus offer a varied range of specific UV filters which can also exhibit various degrees of absorbance. The combination of several of these filters selected according to their specificity and their degree of absorbance thus makes it possible to prepare all types of UV filters acting in the spectrum and with the absorbance desired.

These novel derivatives also have the advantage of being soluble in various pharmaceutically acceptable excipients and of exhibiting better photostability than certain commercial filters, which makes them particularly useful in cosmetic products, notably in sun protectors.

The present invention has as an object the 5,6-diphenyl-1,2,4-triazinic compounds of general formula (I):

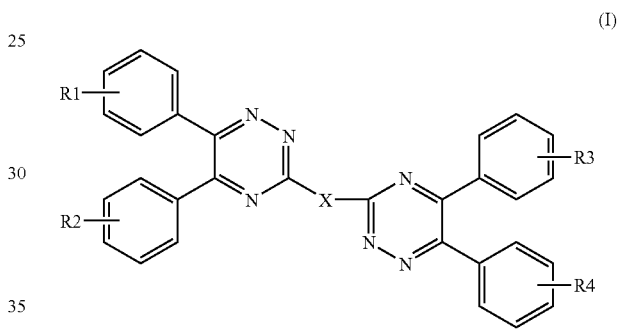

(I)

wherein:
R$_1$, R$_2$, R$_3$ and R$_4$, identical or different, represent a hydrogen, fluorine, chlorine or bromine atom, a C$_1$ to C$_{12}$ linear or branched alkyl group, a hydroxy group, a C$_1$ to C$_{18}$ linear or branched alkoxy group, a poly(ethoxy)-alkoxy group with a C$_1$ to C$_4$ alkyl fragment and an ethoxy number ranging from 1 to 4, an amino group, or a mono- or di-alkylamino group with a C$_1$ to C$_4$ alkyl fragment, X represents an ortho-, meta- or para-phenylene group, a 4,4'-biphenylene group, a 2,4- or 2,6- or 3,4- or 3,5-pyridinylene group, a 2,2'-bipyridinylene group, a meta- or para-phenylenediamino group, an ethylenediamino group, a 2,2'-piperazinylene group, a diacyl group of formula —(R$_4$CO)$_2$— wherein R$_4$ represents a phenyl radical, an alkylated chain of 3 to 10 carbon atoms, phenanthrene or anthracene, with the exception of 1,4-bis(5,6-diphenyl-1,2,4-triazin-3-yl)benzene (X=para-phenylene; R$_1$, R$_2$, R$_3$, R$_4$=—H), 2,4-bis(5,6-diphenyl-1,2,4-triazin-3-yl)pyridine, and 2,6-bis(5,6-diphenyl-1,2,4-triazin-3-yl)pyridine.

Among the compounds of general formula (I), the following compounds have led to particularly advantageous practical results:

R$_1$, R$_2$, R$_3$ and R$_4$ represent a C$_1$ to C$_{12}$ linear or branched alkyl group located in the para position, or a C$_1$ to C$_{18}$ linear or branched alkoxy group located in the para position, and X represents a 4,4'-biphenylene group.

The present invention also has as an object cosmetic sunscreen compositions containing an effective quantity of at least one compound of formula (I) in combination with a cosmetically acceptable excipient, preferably between 0.1% and 20% by weight with respect to the total weight of the composition.

The cosmetic sunscreen compositions according to the invention may contain in addition one or more sun filters active in UV-A and/or UV-B and/or UV-C (absorbers), either hydrophilic or lipophilic. These additional filters may be selected among, in particular, cinnamic derivatives, dibenzoylmethane derivatives, salicylic derivatives, camphor derivatives and triazine derivatives other than those previously cited in the present invention.

The present invention also has as an object the use, as sun filters active in UV-A and/or UV-B and/or UV-C for human skin and/or hair, of 5,6-diphenyl-1,2,4-triazinic compounds of general formula (I):

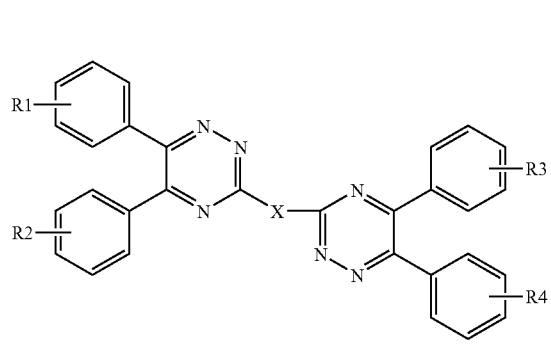

(I)

wherein:
- $R_1$, $R_2$, $R_3$ and $R_4$, identical or different, represent a hydrogen, fluorine, chlorine or bromine atom, a $C_1$ to $C_{12}$ linear or branched alkyl group, a hydroxy group, a $C_1$ to $C_{18}$ linear or branched alkoxy group, a poly(ethoxy)-alkoxy group with a $C_1$ to $C_4$ alkyl fragment and an ethoxy number ranging from 1 to 4, an amino group, or a mono- or di-alkylamino group with a $C_1$ to $C_4$ alkyl fragment,
- X represents an ortho-, meta- or para-phenylene group, a 4,4'-biphenylene group, a 2,4- or 2,6- or 3,4- or 3,5-pyridinylene group, a 2,2'-bipyridinylene group, a meta- or para-phenylenediamino group, an ethylenediamino group, a 2,2'-piperazinylene group, a diacyl group of formula —$(R_4CO)_2$— wherein $R_4$ represents a phenyl radical, an alkylated chain of 3 to 10 carbon atoms, phenanthrene or anthracene.

The present invention also has as an object the use of compounds such as previously defined as light-protective agents active in the UV-A and/or UV-B and/or UV-C spectra, useful in the synthetic materials industry, in particular as light-protective agents incorporated into the composition of plastics, glass or textiles.

These compounds, which are objects of the present invention, can thus be used to protect photosensitive materials.

The light-protective agent could be incorporated into a substratum with the goal of protecting said substratum against attack from ultraviolet rays, to prevent the modification of one or several physical properties of said substratum, such as, for example, discoloration, a change in resistance to tearing, an increase in brittleness, etc., and/or to prevent chemical reactions caused by ultraviolet rays, for example the oxidation process. In this case, the protective agent can be incorporated before and during the preparation of the substratum, or at a later time by a suitable process, for example a binding process analogous to dyeing.

The light-protective agent can also be incorporated into a substratum to protect one or more additional substances incorporated into the aforesaid substratum, for example dyes, auxiliary agents, etc.

The light-protective agent can also be incorporated into a filter layer that may be a solid (film, sheet) or semi-solid (cream, oil, wax) applied to a substratum for the purpose of protecting said substratum from ultraviolet rays.

The compounds of the present invention are suitable not only as light-protective agents for colorless materials, but also for pigmented materials. In this case, the protection against light is extended to the coloring agents, thus allowing in many cases a quite notable improvement of stability in light.

The compounds of general formula (I) can be prepared from 1,2-diketones of formula (II), by conventional methods known to those skilled in the art, such as those described in the examples which follow.

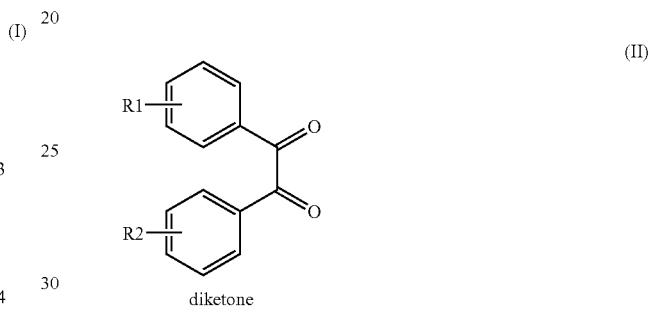

(II)

diketone in which $R_1$ and $R_2$ have the same significance as that given previously.

The diketones of formula (II) are available commercially (such as, for example, benzyl(diphenylethan-1,2-dione), 4,4'-dimethylbenzyl, 4,4'-dibromobenzyl, 4,4'-difluorobenzyl or 4,4'-dichlorobenzyl) or can be synthesized by conventional methods well known to those skilled in the art. For example, the following synthesis route can be used:

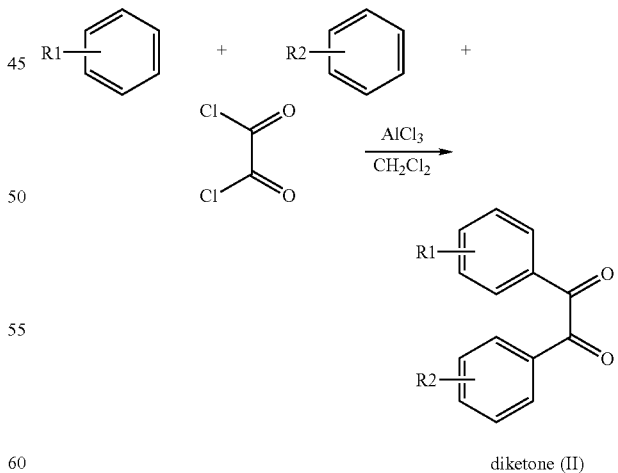

diketone (II)

The examples which follow give other examples of syntheses of diketones of formula (II).

The present invention will be illustrated below by mentioning several nonrestrictive examples of the preparation of representative derivatives conforming to general formula (I).

The compounds prepared are summarized in table 1.

TABLE 1

(I)

[Structure: 1,2,4-triazine dimer connected by X linker, with R1, R2 on one triazine phenyl groups and R3, R4 on the other]

(wherein R$_1$, R$_2$, R$_3$ and R$_4$ are in the para position)

| Reference | X | R$_1$, R$_2$, R$_3$, R$_4$ |
|---|---|---|
| WP30 | –C$_6$H$_4$– (para-phenylene) | H |
| WP35 | –C$_6$H$_4$– | OH |
| WP38 | –C$_6$H$_4$– | Me—(CH$_2$)$_{17}$—O— |
| WP39 | –C$_6$H$_4$– | Me |
| WP40 | –C$_6$H$_4$– | MeO— |
| WP41 | –C$_6$H$_4$– | MeO—(OCH$_2$—CH$_2$)$_4$— |
| WP52 | –C$_6$H$_4$– | Br |
| WP89 | –C$_6$H$_4$– | F |
| WP96 | –C$_6$H$_4$– | Me—(CH$_2$)$_5$— |
| WP100 | –C$_6$H$_4$– | Cl |
| WP104 | –C$_6$H$_4$– | tert-Bu |
| WP107 | –C$_6$H$_4$– | Me—(CH$_2$)$_{11}$— |

TABLE 1-continued

(wherein R₁, R₂, R₃ and R₄ are in the para position)

| Reference | X | R₁, R₂, R₃, R₄ |
|---|---|---|
| WP144 |  | Me—(CH₂)₃—CH(Et)—CH₂—O— |
| WP149 |  | Me—(CH₂)₅—CH(Me)—O— |
| WP151 | 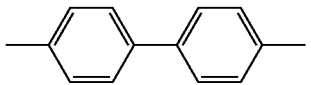 | Me—CH(Me)—(CH₂)₂—CH(Me)₂— |
| WP135 | 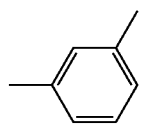 | —H |
| WP76 | 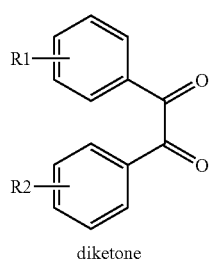 | —H |

The compounds of formula (I) of table 1 can be synthesized in the following way:

wherein R1, R2=hydrogen, halogen,

—OH, $C_1$ to $C_{18}$ linear or branched alkoxy (such as —OMe), $C_1$ to $C_{12}$ linear or branched alkyl, mono- or di-alkylamino with a $C_1$ to $C_4$ alkyl fragment (such as —N(Et)₂).

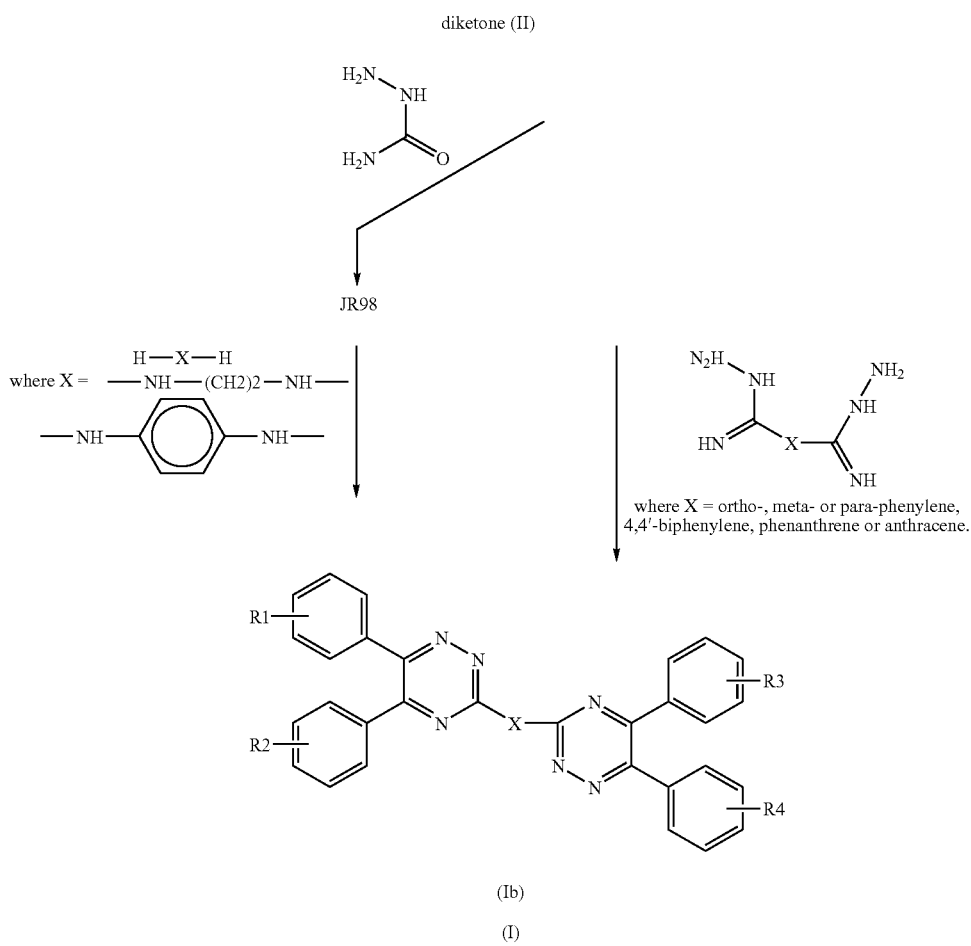

FIGURES

DMB=Parsol 1798® (Roche Laboratories)
MCX=Parsol MCX® (Roche Laboratories)

EXAMPLE 1

Synthesis of 1,2-bis(4-methoxyphenyl)-ethane-1,2-dione[1]

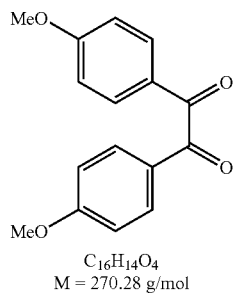

Figure 1:
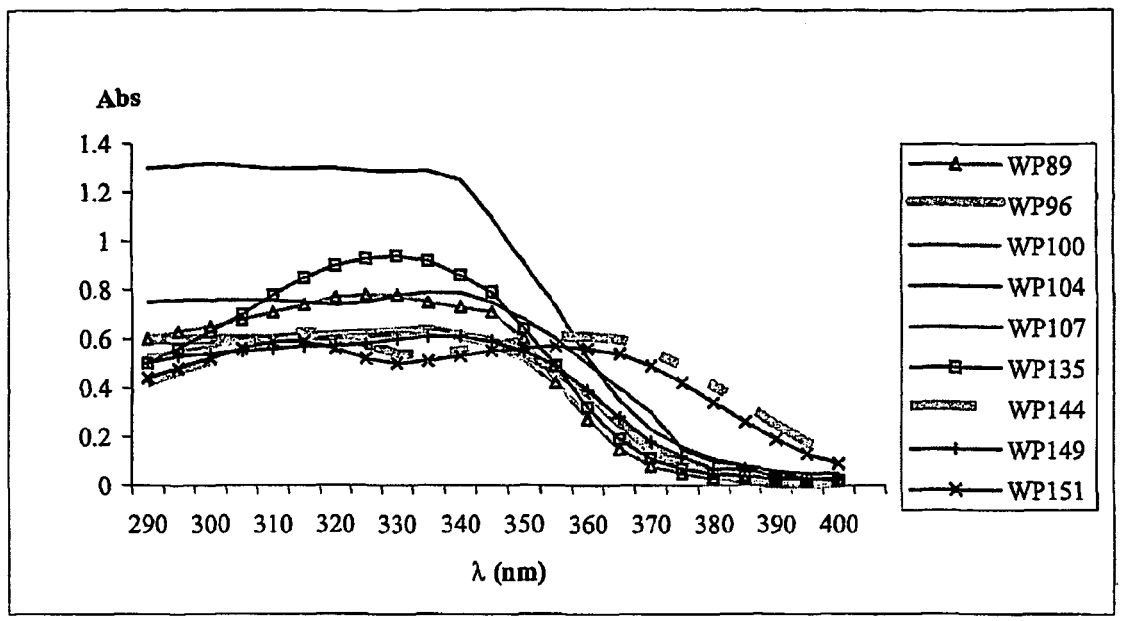
FIG. 1 represents the UV-A and UV-B absorption spectra of compounds WP89, WP96, WP100, WP104, WP107, WP135, WP144, WP149 and WP151.

$C_{16}H_{14}O_4$
M = 270.28 g/mol

Oxalyl chloride (4.71 ml, 55.2 mmol) at 0° C. is slowly added to a mixture of anisole (10.8 g, 100 mmol) and aluminum chloride (33.33 g, 250 mmol). The mixture is stirred at ambient temperature for 4 hours. After cooling, it is poured into iced water and extracted with dichloromethane. The organic phases collected are washed with 2 N HCl then with brine and are dried on magnesium sulfate. After filtration and concentration under reduced pressure, the residue is recrystallized in ethanol. The resulting precipitate is filtered, washed several times in ethanol and dried to yield 9.80 g (66%) of pure product in the form of a yellow solid. $\delta_H$ (200 MHz, CDCl$_3$) 3.93 (s; 6H), 6.99 (d; J 7.8; 4H), 7.99 (d; J 7.8; 4H).

EXAMPLE 2

Synthesis of Diethyl Terephthalimidate[2] (WP18)

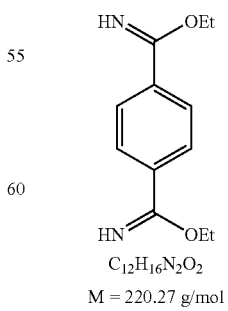

$C_{12}H_{16}N_2O_2$
M = 220.27 g/mol

A suspension of terephthalonitrile (12.81 g, 100 mmol) in absolute ethanol (250 ml) cooled to 0° C. is bubbled with HCl gas for 18 hours, during which the temperature rises to ambient temperature. The white solid obtained (27.5 g of dichlorohydrate salt) is then filtered and washed with ethanol. The neutralization of this salt, dissolved in a minimum of water at 0° C., is carried out by adding a potash solution (15% aqueous) up to basic pH. A white solid is obtained (yield>90%) after filtration, successive washes with water then with pentane and drying. mp 158-161° C.; $\delta_H$ (300 MHz, CDCl$_3$) 1.43 (t; J 7.2; 6H), 4.32 (q; J 7.2; 4H), 7.79 (s; 4H); SM (Electrospray) m/z 222 (40%), 221 (MH$^+$, 100%), 193 (M-CH=CH$_2$, 42%).

EXAMPLE 3

Synthesis of Terephthalamidrazone[(2)] (WP29)

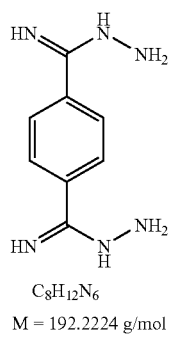

C$_8$H$_{12}$N$_6$
M = 192.2224 g/mol

Hydrazine monohydrate (6.55 ml; 135 mmol) is added over the course of 10 minutes to a suspension of WP18 prepared according to example 2 (9.92 g, 45.035 mmol) in absolute ethanol (75 ml). The mixture quickly becomes homogeneous, then a yellow precipitate slowly forms. After 24 hours, the precipitate is filtered, washed successively with ethanol then with diethyl ether and is dried to yield 6.838 g (79%) of a yellow solid. $\delta_H$ (300 MHz, D$_2$O) 7.66 (s; 4H).

EXAMPLE 4

Synthesis of 1,4-bis(5,6-diphenyl-1,2,4-triazin-3-yl)benzene[(3)] (WP30)

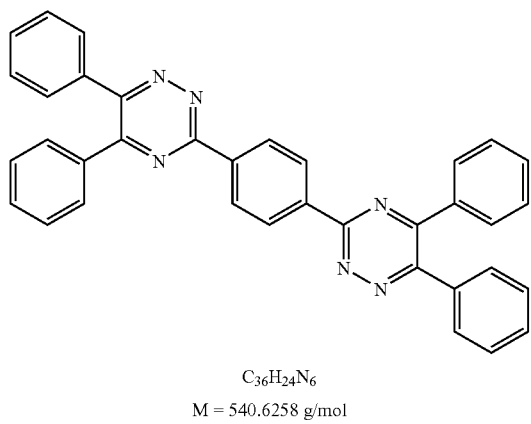

C$_{36}$H$_{24}$N$_6$
M = 540.6258 g/mol

Terephthalamidrazone WP29 prepared according to example 3 (1.00 g, 5.203 mmol) is added all at once to a solution of benzyl (2.455 g, 11.67 mmol) in ethanol (100 ml). The mixture is heated at reflux for 15 hours. After returning to ambient temperature, the precipitate obtained is filtered, washed successively with ethanol then with diethyl ether and is dried to yield 2.587 g (92%) of a yellow solid. mp=321° C.; $\delta_H$ (300 MHz, DMSO-d, 120° C.) 7.42-7.52 (m; 12H), 7.62 (m; 4H), 7.71 (m; 4H), 8.81 (s; 4H); $\delta_C$ (75 MHz, DMSO-d, 120° C.) 129.2 (1), 129.3 (1), 130.2 (1), 130.3 (1), 130.5 (1), 131.4 (1), 136.5 (0), 136.6 (0), 138.4 (0), 156.5 (0), 156.9 (0), 161.3 (0); MS (Nanospray) m/z 1081 (2M+H$^+$, 22%), 541 (MH$^+$, 41%).

EXAMPLE 5

Synthesis of 4,4'-dihydroxybenzyl[(4)] (WP32)

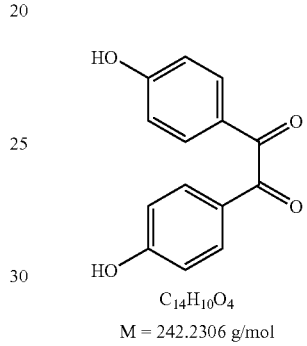

C$_{14}$H$_{10}$O$_4$
M = 242.2306 g/mol

A mixture of 1,2-bis(4-methoxyphenyl)-ethane-1,2-dione prepared according to example 1 (7.275 g, 26.91 mmol) and pyridine hydrochlorate (15.55 g, 134.5 mmol) under an atmosphere of nitrogen is heated to 180° C. for 2 days. After returning to ambient temperature, the mixture is diluted with ethyl acetate and water. The aqueous phase is extracted with ethyl acetate and the recombined organic phases are dried on magnesium sulfate, filtered and concentrated under reduced pressure. The residue is purified by flash chromatography on a silica gel (petroleum ether/ethyl acetate 10/1 to 2/1) to yield 5.789 g (89%) of a white solid. $\delta_H$ (300 MHz, MeOH-d) 6.91 (d; J 9.0; 4H), 7.82 (d; J 9.0; 4H).

EXAMPLE 6 p-Tosylate of 2-{2-[2-(2-methoxy-ethoxy)-ethoxy]-ethoxy}-ethyl[(5)] (WP33)

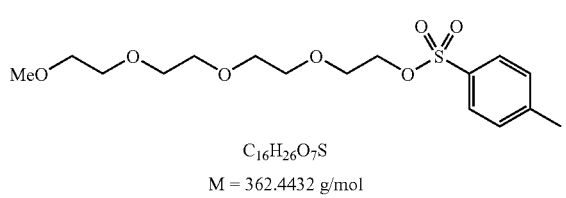

C$_{16}$H$_{26}$O$_7$S
M = 362.4432 g/mol

To a mixture of tetraethylene glycol monomethyl ether (3.00 g, 14.406 mmol) and soda (0.865 g, 21.6 mmol) diluted in THF (33 ml) and water (4 ml) cooled to 0° C., a solution of p-toluenesulfonic acid chloride (3.021 g, 15.8 mmol) in THF (4 ml) is slowly added. After 3 hours of stirring at 0° C., the mixture is poured into iced water (10 ml) and is diluted by dichloromethane. The aqueous phase is extracted with dichloromethane and the recombined organic phases are washed with water then with a NaCl-saturated solution, dried on MgSO$_4$, filtered and concentrated under reduced pressure. The residue is purified by flash chromatography on a silica gel (petroleum ether/ethyl acetate 1/1 to 1/4) to yield 4.234 g (82%) of a colorless oil. $\delta_H$ (300 MHz, CDCl$_3$) identical to the literature.

EXAMPLE 7

Synthesis of 1,4-bis[5,6-(4,4'-dihydroxy)-diphenyl-1,2,4-triazin-3-yl]benzene (WP35)

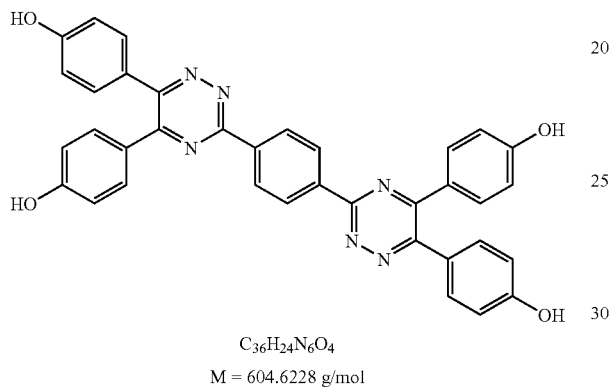

C$_{36}$H$_{24}$N$_6$O$_4$
M = 604.6228 g/mol

To a solution of WP32 prepared according to example 5 (600 mg, 2.47 mmol) in ethanol (20 ml), terephthalamidrazone WP29 prepared according to example 3 (190 mg, 0.991 mmol) is added all at once. The mixture is heated at reflux for 15 hours. After returning to ambient temperature, the precipitate obtained is filtered, successively washed with ethanol then with diethyl ether and is dried to yield 479 mg (80%) of a yellow solid. $\delta_H$ (300 MHz, DMSO-d, 25° C.) 6.79-6.84 (m; 8H), 7.44 (d; J 8.4; 4H), 7.58 (d; J 8.4; 4H), 8.71 (s; 4H), 10.03 (sl; 4H); MS (Nanospray) m/z 605 (MH$^+$, 53%)

EXAMPLE 8

Synthesis of 1,2-bis-[4-(2-{2-[2-(2-methoxy-ethoxy)-ethoxy]-ethoxy}-ethoxy)phenyl]-ethane-1,2-dione (WP36)

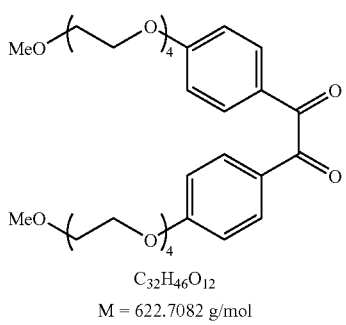

C$_{32}$H$_{46}$O$_{12}$
M = 622.7082 g/mol 1,2-bis(4-methoxyphenyl)-ethane-1,2-dione prepared according to example 1 (1.135 g, 4.687 mmol) and then potassium carbonate (3.239 g, 23.4 mmol) are added successively to a solution of tosylate WP33 prepared according to example 6 (3.737 g, 10.3 mmol) in DMF (50 ml). The mixture is stirred at 50° C. for 4 hours. After returning to ambient temperature, the mixture is poured into iced water and extracted several times with ethyl acetate. The recombined organic phases are washed several times with a NaHCO$_3$—saturated solution, then with brine. After drying on MgSO$_4$, filtration and concentration under reduced pressure, the residue obtained is purified by flash chromatography on a silica gel (ethyl acetate, then dichloromethane/methanol 1% to 1.5%) to yield 1.568 g (54%, not optimized) of a yellow oil. $\delta_H$ (300 MHz, CDCl$_3$) 3.36 (s; 6H), 3.51 (m; 4H), 3.51-3.71 (m; 20H), 3.87 (m; 4H), 4.19 (m; 4H), 6.97 (d, J 8.8; 4H), 7.92 (d, J 8.8; 4H); MS (Electrospray) m/z 623 (MH$^+$, 100%).

EXAMPLE 9

Synthesis of 1,2-bis-(4-octadecyloxy-phenyl)-ethane-1,2-dione[6] (WP37)

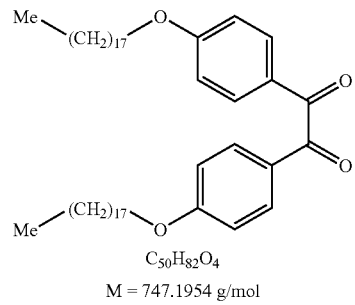

C$_{50}$H$_{82}$O$_4$
M = 747.1954 g/mol

Soda (726 mg, 18.1 mmol) is added to a solution of 1,2-bis(4-methoxyphenyl)-ethane-1,2-dione prepared according to example 1 (2.00 g, 8.25 mmol) in DMF (50 ml). The mixture is stirred for 5 minutes at ambient temperature, then 1-iodooctadecane (9.4 g, 24.7 mmol) is added over the course of 1 minute. After 3 hours of stirring to 60° C., the mixture is cooled. The precipitate obtained is filtered, washed successively with DMF then with ethanol and dried under a vacuum to yield 3.792 g (61%) of a white solid. mp 87° C.; $\delta_H$ (300 MHz, C$_6$D$_6$) 0.90 (t; J 6.0; 6H), 1.18-1.42 (m; 60H), 1.51 (m; 4H), 3.46 (t; J 6.5; 4H), 6.64 (d; J 9.0; 4H), 8.09 (d; J 9.0; 4H); MS (Electrospray) m/z 1493 (2M+H$^+$, 5%), 747 (MH$^+$, 26%).

EXAMPLE 10

Synthesis of 1,4-bis[5,6-(4,4'-di-octadecyloxy)-diphenyl-1,2,4-triazin-3-yl]benzene (WP38)

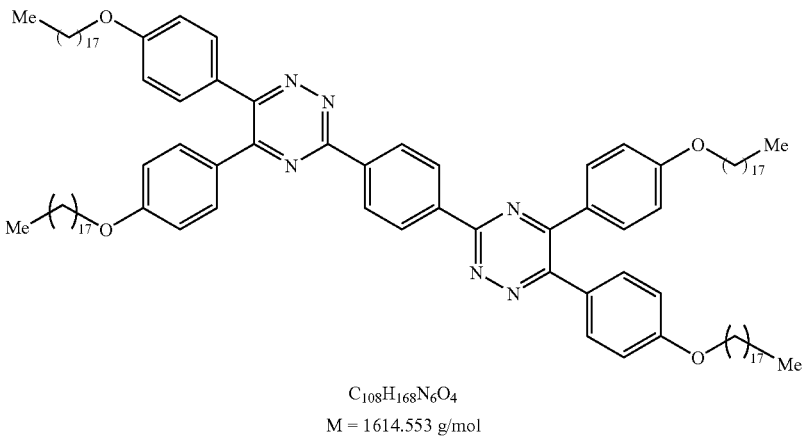

C₁₀₈H₁₆₈N₆O₄
M = 1614.553 g/mol

Terephthalamidrazone WP29 prepared according to example 3 (200 mg, 1.04 mmol) in ethanol (20 ml) is added all at once to a solution of WP37 prepared according to example 9 (1.71 g, 22.88 mmol). The mixture is heated at reflux for 15 hours. After returning to ambient temperature, the precipitate obtained is filtered and washed with ethanol, then purified by flash chromatography on a silica gel (toluene, then toluene/methanol 1% to 2%) to yield 1.409 g (84%) of a yellow solid. $\delta_H$ (300 MHz, C₆D₆) 0.91 (m; 6H), 1.18-1.42 (m; 120H), 1.51 (m; 8H), 3.60 (m; 8H), 6.75 (d; J 9.0; 4H), 6.81 (d; J 9.0; 4H), 7.71 (d; J 9.0; 4H), 7.73 (d; J 9.0; 4H), 9.22 (s; 4H); MS (Electrospray) m/z 1615 (MH⁺, 64%), 1614 (75%), 890 (100%).

EXAMPLE 11

Synthesis of 1,4-bis[5,6-(4,4'-dimethyl)-diphenyl-1,2,4-triazin-3-yl]benzene (WP39)

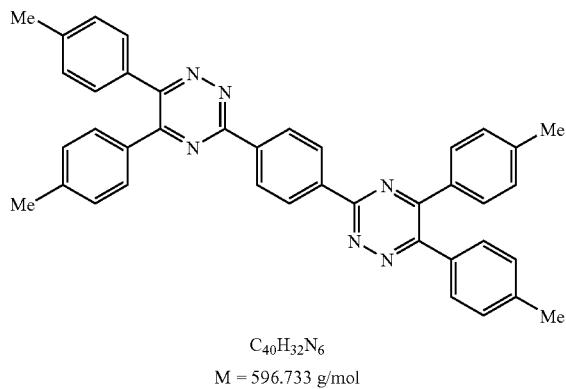

C₄₀H₃₂N₆
M = 596.733 g/mol

Terephthalamidrazone WP29 prepared according to example 3 (1.50 g, 7.804 mmol) is added all at once to a solution of 4,4'-dimethylbenzyl (4.091 g, 17.16 mmol) in ethanol (140 ml). The mixture is heated at reflux for 15 hours. After returning to ambient temperature, the precipitate obtained is filtered, washed successively in ethanol then with diethyl ether and is dried to yield 4.42 g (95%) of a yellow solid. $\delta_H$ (300 MHz, DMSO-d, 120° C.) 2.50 (s; 12H), 7.27 (m; 8H), 7.52 (d; J 8.0; 4H), 7.61 (d; J 8.0; 4H), 8.78 (s; 4H); MS (Nanospray) m/z 1789 (3M+H⁺, 65%), 1193 (2M+H⁺, 57%), 597 (MH⁺, 49%).

EXAMPLE 12

Synthesis of 1,4-bis[5,6-(4,4'-dimethoxy)-diphenyl-1,2,4-triazin-3-yl]benzene (WP40)

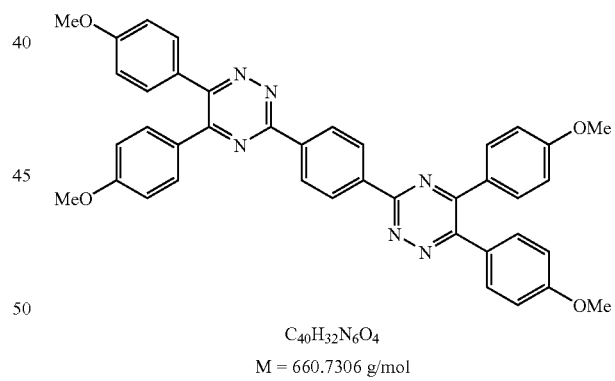

C₄₀H₃₂N₆O₄
M = 660.7306 g/mol

Terephthalamidrazone WP29 prepared according to example 3 (1.50 g, 7.804 mmol) is added all at once to a solution of 1,2-bis(4-methoxyphenyl)-ethane-1,2-dione prepared according to example 1 (5.273 g, 19.5 mmol) in ethanol (140 ml). The mixture is heated at reflux for 30 hours. After returning to ambient temperature, the precipitate obtained is filtered, washed successively with ethanol, dichloromethane and diethyl ether then dried to yield 4.087 g (80%) of a yellow solid. $\delta_H$ (300 MHz, DMSO-d, 120° C.) 3.86 (s; 12H), 7.02 (m; 8H), 7.58 (d; J 7.8; 4H), 7.71 (d; J 8.7; 4H), 8.77 (s; 4H); MS (Nanospray) m/z 661 (MH⁺, 8%), 332 (55%).

EXAMPLE 13

Synthesis of 1,4-bis[5,6-(4,4'-(2-{2-[2-(2-methoxy-ethoxy)-ethoxy]-ethoxy}-ethoxy)-)-diphenyl-1,2,4-triazin-3-yl]benzene (WP41)

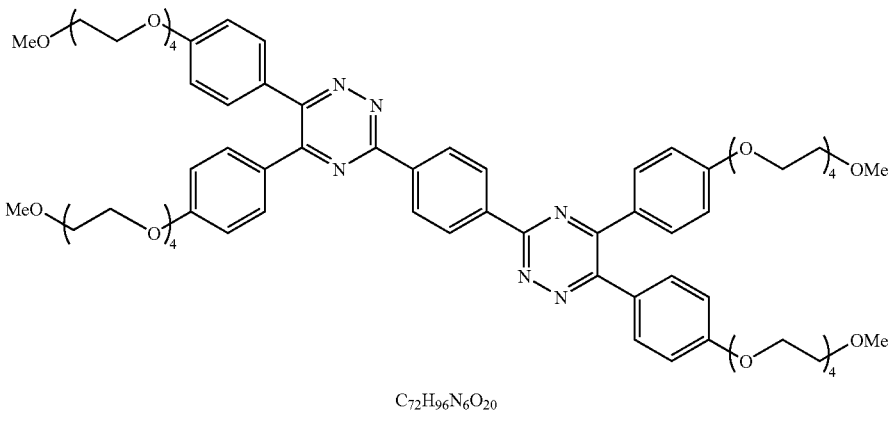

C$_{72}$H$_{96}$N$_6$O$_{20}$
M = 1365.5786 g/mol

Terephthalamidrazone WP29 prepared according to example 3 (64 mg, 0.337 mmol) is added all at once to a solution of WP36 prepared according to example 8 (524 mg, 0.842 mmol) in ethanol (7 ml). The mixture is heated at reflux for 30 hours. After returning to ambient temperature, the solvent is concentrated under reduced pressure and the residue is purified directly by flash chromatography on a silica gel (ethyl acetate, then ethyl acetate/methanol 2% to 6%) to yield 350 mg (76%) of a yellow solid. δ$_H$ (300 MHz, CDCl$_3$) 3.37 (s; 12H), 3.54 (m; 8H), 3.60-3.74 (m; 40H), 3.88 (m; 8H), 4.18 (m; 8H), 6.93 (m; 8H), 7.60 (d, J 8.8; 4H), 7.92 (d, J 8.8; 4H); 8.82 (s; 4H); δ$_C$ (75 MHz, CDCl$_3$) 58.9 (3), 67.3 (2), 67.4 (2), 69.4 (2), 69.5 (2), 70.4 (2), 70.5 (2), 70.7 (2), 71.8 (2), 114.5 (1), 114.6 (1), 128.0 (1), 128.1 (1), 128.4 (1), 130.6 (1), 131.4 (1), 137.5 (1), 154.2 (0), 154.7 (0), 159.9 (0), 160.1 (0), 160.9 (0); MS (Electrospray) m/z 1387 (M+Na$^+$, 24%), 1366 (MH$^+$, 100%).

EXAMPLE 14

Synthesis of 1,4-bis[5,6-(4,4'-dibromo)-diphenyl-1,2,4-triazin-3-yl]benzene (WP52)

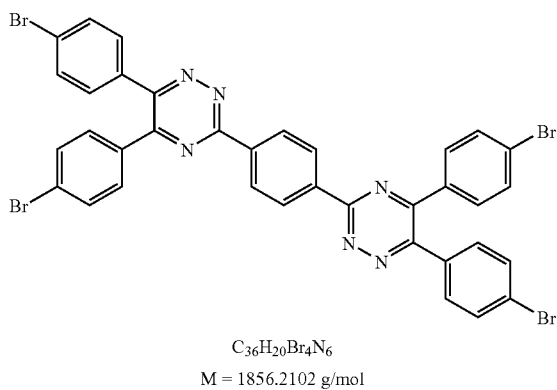

C$_{36}$H$_{20}$Br$_4$N$_6$
M = 1856.2102 g/mol

Terephthalamidrazone WP29 prepared according to example 3 (200 mg, 1.040 mmol) is added all at once to a solution of 4,4'-dibromobenzyl (1.149 g, 3.12 mmol) in ethanol (20 ml). The mixture is heated at reflux for 15 hours. After returning to ambient temperature, the precipitate obtained is filtered, washed successively with ethanol, dichloromethane and diethyl ether then dried to yield 757 mg (85%) of a yellow solid. <δ$_H$ (300 MHz, DMSO-d, 120° C.) 7.56-7.69 (m; 8H), 7.80-7.88 (m; 8H), 8.80 (s; 4H).

EXAMPLE 15

Synthesis of 4-bromododecanoylbenzene[7] (WP59)

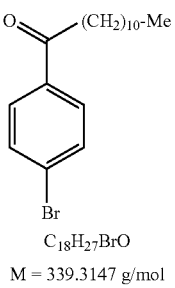

C$_{18}$H$_{27}$BrO
M = 339.3147 g/mol

Dodecanoyl chloride (44.1 ml, 191.1 mmol) is slowly added to a mixture of bromobenzene (60 g, 382.1 mmol) and aluminum chloride (30.57 g, 229.3 mmol). The mixture is stirred at 50° C. for 1 hour. After cooling, the mixture is poured into iced water and extracted with dichloromethane. The recombined organic phases are washed with 2 N HCl then with brine and are dried on magnesium sulfate. After filtration and concentration under reduced pressure, the residue is taken up in ethanol. The resulting precipitate is filtered, washed several times in ethanol and dried to yield 36.9 g (57%, not optimized) of pure product in the form of a white solid (no recrystallization). Analyses identical to the literature.

EXAMPLE 16

Synthesis of 4-bromododecylbenzene[7] (WP60)

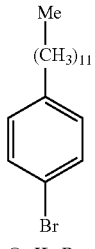

C$_{18}$H$_{29}$Br
M = 325.3311 g/mol$^{-1}$

Hydrazine monohydrate (23.6 ml, 4.5 eq) and then potash (24.3 g, 4 eq) are added to a solution of WP59 prepared according to example 15 (36.5 g, 108.87 mmol) in tri(ethylene glycol) (180 ml). The mixture is stirred at reflux for approximately 15 hours. After cooling, it is poured into water, acidified with concentrated HCl, then extracted with dichloromethane. The organic phase is washed with water, dried on magnesium sulfate, filtered and concentrated under reduced pressure. The residue is purified by flash chromatography on a silica gel (pentane 100%) to yield 21.2 g (60%, not optimized) of a colorless oil. Analyses identical to the literature.

EXAMPLE 17

Synthesis of Diethyl Isophthalimidate (WP73)

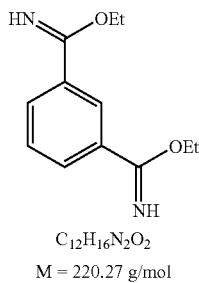

$C_{12}H_{16}N_2O_2$

M = 220.27 g/mol

A suspension of isophthalonitrile (12.81 g, 100 mmol) in a mixture of dry 1,4-dioxane (100 ml)/absolute ethanol (14.6 ml) cooled to 0° C. is bubbled with HCl gas for 48 hours, during which time the temperature returns to ambient temperature. After 4 additional days of stirring, the white solid obtained (approximately 28 grams of di-chlorhydrate salt) is filtered and washed with diethyl ether. The neutralization of this salt placed in suspension in diethyl ether is carried out by slowly adding potassium an aqueous carbonate solution (30% by weight) up to basic pH. The organic phase is separated, dried on MgSO$_4$, filtered and concentrated under reduced pressure to yield a white solid (yield>90%). $\delta_H$ (300 MHz, CDCl$_3$) 1.44 (t; J 6.9; 6H), 4.32 (q; J 6.9; 4H), 7.47 (t; J 7.5; 1H), 7.86 (d; J 7.5; 2H), 8.16 (s; 1H); SM (Electrospray) m/z 221 (MH$^+$, 100%).

EXAMPLE 18

Synthesis of Isophthalamidrazone[8] (WP75)

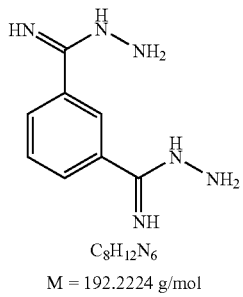

$C_8H_{12}N_6$

M = 192.2224 g/mol

Hydrazine monohydrate (485 µl, 9.98 mmol) is added over the course of 10 minutes to a suspension of diethyl isophthalimidate WP73 prepared according to example 17 (1.0 g, 4.53 mmol) in dry acetonitrile (18 ml) cooled to 0° C. After 48 hours of stirring, the precipitate formed is filtered, washed with acetonitrile and dried to yield 630 mg (72%) of a yellow solid. $\delta_H$ (300 MHz, D$_2$O) 7.50 (t; J 7.3; 1H), 7.67 (d; J 7.3; 2H), 7.80 (s; 1H); SM (in solution in D$_2$O) (EI) m/z 199 (100%).

EXAMPLE 19

Synthesis of 1,3-bis(5,6-diphenyl-1,2,4-triazin-3-yl)benzene (WP76)

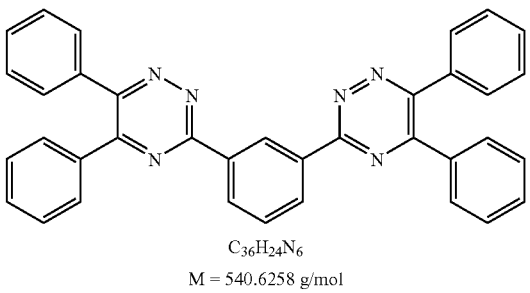

$C_{36}H_{24}N_6$

M = 540.6258 g/mol

WP75 prepared according to example 18 (620 mg, 3.225 mmol) is added all at once to a solution of benzyl (1.491 g, 7.09 mmol) in ethanol (60 ml). The mixture is heated at reflux for 20 hours. After returning to ambient temperature, the precipitate obtained is filtered, washed successively with ethanol then with diethyl ether and is dried to yield 1.488 g (85%) of a yellow solid. $\delta_H$ (300 MHz, DMSO-d, 120° C.) 7.42-7.52 (m; 12H), 7.61 (d; J 1.2; 4H), 7.63 (d; J 1.5; 4H), 7.90 (t; J 7.3; 1H), 8.81 (d; J 7.3; 2H), 9.77 (s; 1H); MS (Electrospray) m/z 1081 (2M+H$^+$, 74%), 541 (MH$^+$, 100%), 175 (88%).

EXAMPLE 20

Synthesis of 1,4-bis[5,6-(4,4'-difluoro)-diphenyl-1,2,4-triazin-3-yl]benzene (WP89)

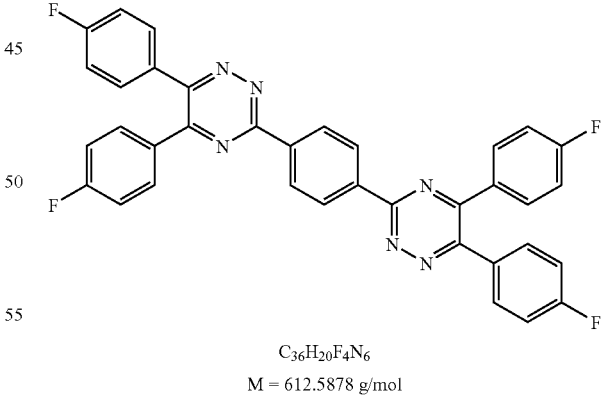

$C_{36}H_{20}F_4N_6$

M = 612.5878 g/mol

Terephthalamidrazone WP29 prepared according to example 3 (200 mg, 1.040 mmol) is added all at once to a solution of 4,4'-difluorobenzyl (769 mg, 3.12 mmol) in ethanol (20 ml). The mixture is heated at reflux for 15 hours. After returning to ambient temperature, the precipitate obtained is filtered, washed successively with ethanol then with diethyl ether and is dried under a vacuum to yield 541 mg (85%) of a yellow solid. $\delta_H$ (300 MHz, DMSO-d, 120° C.) 7.56-7.69 (m;

8H), 7.80-7.88 (m; 8H), 8.80 (s; 4H). MS (Electrospray) m/z 613 (MH⁺, 100%), 178 (34%).

EXAMPLE 21

Synthesis of 1,2-bis(4-hexylphenyl)-ethane-1,2-dione (WP94)

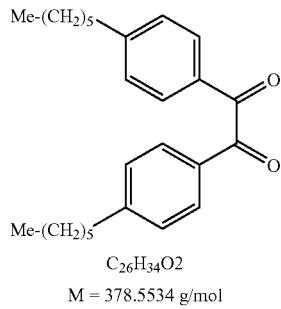

$C_{26}H_{34}O_2$

M = 378.5534 g/mol

A solution of s-BuLi (1.3 M in cyclohexane, 5.4 ml, 7.02 mmol) is slowly added to a solution of 4-bromo-n-hexylbenzene (1.68 g, 7.02 mmol) in THF (9 ml) at −78° C. and under an atmosphere of nitrogen. After one hour of stirring, the mixture is transferred using a cannula to a suspension of 1,4-dimethylpiperazine-2,3-dione (450 mg, 3.166 mmol) in THF (11 ml) cooled to −40° C. After returning to ambient temperature, the mixture is stirred for 15 hours then treated with 5 ml of 2 N HCl. After dilution with dichloromethane and stirring, the organic phase is separated, washed with 2 N HCl then with water, and dried on magnesium sulfate. After filtration and concentration, the residue is purified by flash chromatography on a silica gel (pentane/ethyl acetate 100/0; 4/1; 3/1; 2/1) to yield 820 mg (68%) of a yellow oil. $\delta_H$ (300 MHz, CDCl₃) 0.87 (t; J 6.6; 6H), 1.20-1.40 (m; 12H), 1.50-1.70 (m; 4H), 2.67 (t; J 7.5; 4H), 7.30 (d; J 8.4; 4H), 7.87 (d; J 8.4; 4H); MS (IC) m/z 379 (MH⁺, 100%).

EXAMPLE 22

Synthesis of 1,4-bis[5,6-(4,4'-dihexyl)-diphenyl-1,2,4-triazin-3-yl]benzene (WP96)

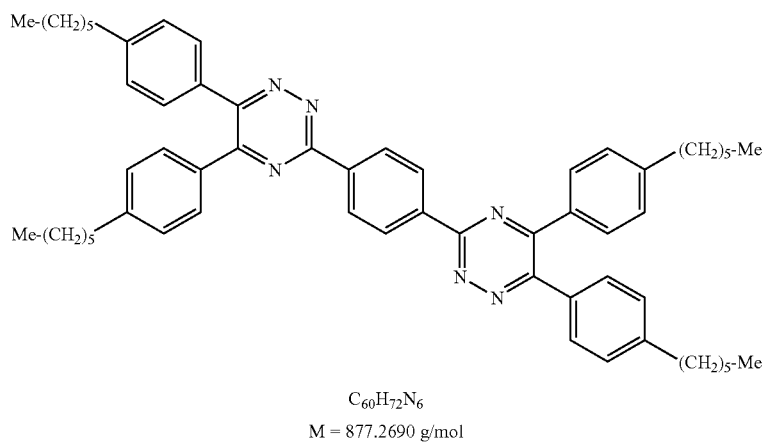

$C_{60}H_{72}N_6$

M = 877.2690 g/mol

Terephthalamidrazone WP29 prepared according to example 3 (43 mg, 0.22 mmol) is added all at once to a solution of WP94 prepared according to example 21 (187 mg, 0.49 mmol) in ethanol (5 ml). The mixture is heated at reflux for 15 hours. After returning to ambient temperature, the precipitate obtained is filtered, washed with ethanol and dried to yield 144 mg (74%) of a yellow solid. $\delta_H$ (300 MHz, CDCl₃) 0.88 (m; 12H), 1.20-1.40 (m; 24H), 1.45-1.70 (m; 8H), 2.65 (t; J 7.8; 8H), 7.18 (m; 8H), 7.57 (d; J 8.4; 4H), 7.65 (d; J 7.8; 4H); MS (Electrospray) m/z 1754 (2M+H⁺, 33%), 877 (MH⁺, 100%).

EXAMPLE 23

Synthesis of 1,4-bis[5,6-(4,4'-dichloro)-diphenyl-1,2,4-triazin-3-yl]benzene (WP100)

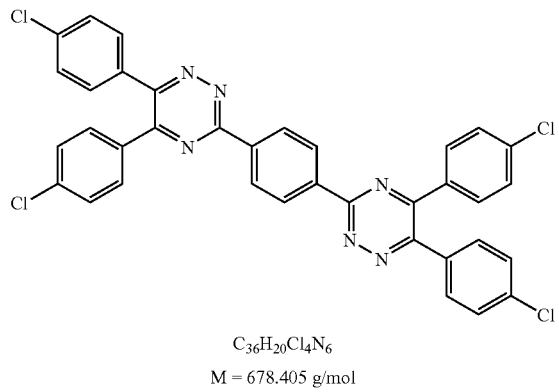

$C_{36}H_{20}Cl_4N_6$

M = 678.405 g/mol

Terephthalamidrazone WP29 prepared according to example 3 (24 mg, 0.122 mmol) is added all at once to a solution of 4,4'-chlorobenzyl (75 mg, 0.27 mmol) in ethanol (3 ml). The mixture is heated at reflux for 15 hours. After returning to ambient temperature, the precipitate obtained is filtered, washed successively with ethanol then with diethyl ether and dried under a vacuum to yield a yellow solid (yield not calculated). $\delta_H$ (300 MHz, DMSO-d, 120° C.) 7.50-7.60 (m; 12H), 7.69 (d; J 8.4; 4H), 8.81 (s; 4H).

EXAMPLE 24

Synthesis of 1,2-bis(4-tert-butyl-phenyl)-2-hydroxy-ethanone (WP101)

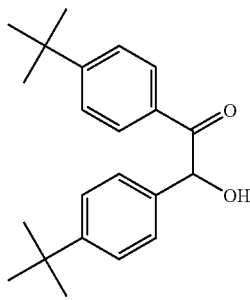

C$_{22}$H$_{28}$O$_2$
M = 324.642 g/mol

A solution of potassium cyanide (4.61 g, 70.89 mmol) in water (14 ml) is slowly added to a solution of 4-tert-butylbenzaldehyde (115 g, 708.9 mmol) in a methanol (300 ml)/water (40 ml) mixture. The mixture is stirred at 90° C. for 40 hours. After cooling, the methanol is concentrated under reduced pressure and the residue is taken up in dichloromethane and water. After three extractions with dichloromethane, the recombined organic phases are dried on magnesium sulfate, filtered and concentrated under reduced pressure. Pentane (approximately 800 ml) is then added, and the resulting precipitate is filtered, washed several times in pentane and dried to yield 55.23 g (49%, not optimized) of pure product in the form of a white solid. Analyses identical to the literature.

EXAMPLE 25

1,2-bis(4-tert-butyl-phenyl)-ethane-1,2-dione (WP103)

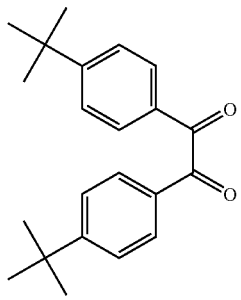

C$_{22}$H$_{26}$O$_2$
M = 322.4462 g/mol

A 15% solution by weight of Dess-Martin periodinane in dichloromethane (100 ml, approximately 46.29 mmol) is added over the course of 10 minutes to a solution of WP101 cooled to 0° C. prepared according to example 24 (12 g, 37.037 mmol) in dry dichloromethane (350 ml). The mixture is stirred overnight, then diluted with dichloromethane and treated with a solution saturated with sodium hydrogen carbonate. After 10 minutes of stirring, the organic phase is separated and the aqueous phase is extracted with dichloromethane. The recombined organic phases are washed with a solution saturated with sodium chloride, filtered and concentrated under reduced pressure. The residue obtained is purified by flash chromatography on a silica gel (pentane/dichloromethane 4/1 to 1.5/1) to yield 10.78 g (90%) of a yellow oil which is solidified under a high vacuum. Analyses identical to the literature.

EXAMPLE 26

Synthesis of 1,4-bis[5,6-(4,4'-4-di-tert-butyl)-diphenyl-1,2,4-triazin-3-yl]benzene (WP104)

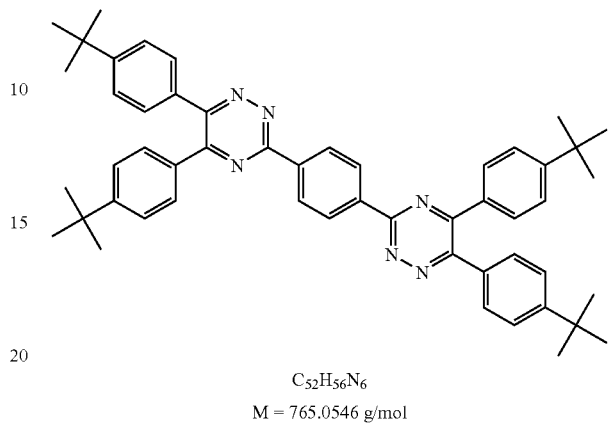

C$_{52}$H$_{56}$N$_6$
M = 765.0546 g/mol

Terephthalamidrazone WP29 prepared according to example 3 (2.924 g, 15.217 mmol) is added all at once to a suspension of WP103 prepared according to example 25 (10.78 g, 33.47 mmol) in ethanol (250 ml). The mixture is heated at reflux for 15 hours. After returning to ambient temperature, the precipitate obtained is filtered, washed with ethanol and dried to yield 10.56 g (93%) of a yellow solid. δ$_H$ (300 MHz, CDCl$_3$) 1.35 (s; 36H), 7.42 (m; 8H), 7.63 (d; J 8.1; 4H), 7.71 (d; J 8.4; 4H), 8.85 (s; 4H); MS (Electrospray) m/z 1789 (3M+H$^+$, 65%), 1530 (2M+H$^+$, 71%), 765 (MH$^+$, 100%).

EXAMPLE 27

Synthesis of 1,2-bis(4-dodecylphenyl)-ethane-1,2-dione[7] (WP105)

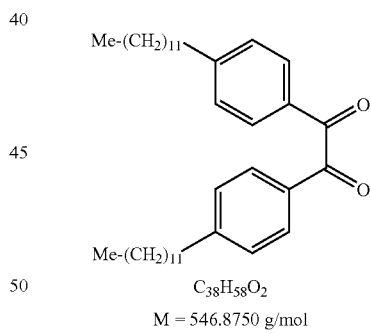

C$_{38}$H$_{58}$O$_2$
M = 546.8750 g/mol

A solution of 4-bromo-dodecylbenzene WP60 prepared according to example 16 (20.19 g, 62.065 mmol) in THF (80 ml) is slowly added to a solution of 30 ml of dry THF and s-BuLi (1.3 M in cyclohexane, 47.7 ml, 62.065 mmol) cooled to −78° C. and under a nitrogen atmosphere. After one hour of stirring, the mixture is transferred using a cannula to a suspension of 1,4-dimethylpiperazine-2,3-dione (107 mg, 0.7539 mmol) in THF (2.7 ml) cooled to −40° C. The mixture is stirred for 15 hours then treated with 2 N HCl. After dilution with dichloromethane and stirring, the organic phase is separated, washed with 2 N HCl then with water, and is dried on magnesium sulfate. After filtration and concentration, the residue is purified by flash chromatography on a silica gel (pentane/ethyl acetate 100/0; 10/1; 4/1; 3/1; 2/1) to yield 2.77 g (18%) of a yellow oil. Analyses identical to the literature.

EXAMPLE 28

Synthesis of 1,4-bis[5,6-bis(4-dodecylphenyl)-1,2,4-triazine-3-yl]benzene (WP107)

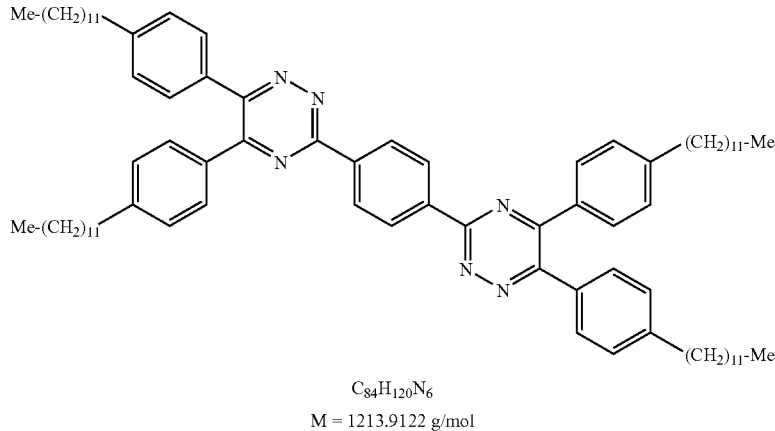

$C_{84}H_{120}N_6$
M = 1213.9122 g/mol

Terephthalamidrazone WP29 prepared according to example 3 (275 mg, 1.431 mmol) is added all at once to a solution of WP105 prepared according to example 27 (1.649 g, 3.147 mmol) in ethanol (70 ml). The mixture is heated at reflux for 15 hours. After returning to ambient temperature, the precipitate obtained is filtered, washed with ethanol and dried to yield 1.38 g (80%) of a yellow solid. $\delta_H$ (300 MHz, CDCl$_3$) 0.87 (m; 12H), 1.20-1.40 (m; 72H), 1.50-1.70 (m; 8H), 2.63 (t; J 7.5; 8H), 7.20 (m; 8H), 7.57 (d; J 8.1; 4H), 7.65 (d; J 8.4; 4H); MS (Electrospray) m/z 1213.9 (MH$^+$, 100%).

EXAMPLE 29

Synthesis of biphenyl-4,4'-diethyldicarboximidate (WP129)

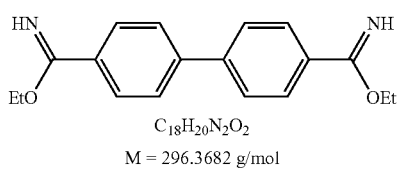

$C_{18}H_{20}N_2O_2$
M = 296.3682 g/mol

A suspension of terephthalonitrile (2.5 g, 12.24 mmol) in absolute ethanol (30 ml) cooled to 0° C. is bubbled with HCl gas for 24 hours, during which time the temperature returns to ambient temperature. The white solid obtained is then filtered and washed with ethanol. The neutralization of this salt dissolved in a minimum of water at 0° C. is carried out by adding a solution of 0° C. K$_2$CO$_3$ (30% by weight) up to basic pH. The white solid obtained is dissolved in dichloromethane. The aqueous phase is separated then the organic phase is dried on MgSO$_4$, filtered and concentrated to yield a white solid (yield>90%). $\delta_H$ (300 MHz, CDCl$_3$) 1.4 (t; J 7.2; 6H), 4.34 (q; J 7.2; 4H), 7.63 (d; J 8.7; 4H), 7.83 (d; J 8.7; 4H).

EXAMPLE 30

Synthesis of 4-(1-oxo-4-methyl-pentyl)bromobenzene[9] (WP132)

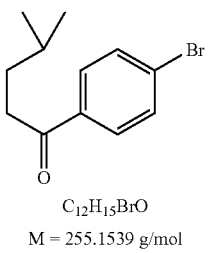

$C_{12}H_{15}BrO$
M = 255.1539 g/mol

A mixture of 4-methyl valeric acid (15 g, 129.1 mmol) and thionyl chloride (10.8 ml, 148 mmol) is heated at reflux for 90 minutes. The excess thionyl chloride is distilled under reduced pressure, then the residue is taken up in 48 ml of bromobenzene. After cooling to 0° C., anhydrous aluminum chloride (13.8 g, 103.5 mmol) is added to the solution. The mixture is stirred at ambient temperature for 80 hours, then treated with the addition of iced water, then with 20 ml of concentrated HCl. The organic phase is separated and the aqueous phase extracted by Et$_2$O. The recombined organic phases are washed successively with water then with a solution saturated with sodium chloride, dried on MgSO$_4$, filtered and concentrated under reduced pressure. The residue is purified either by a) distillation (approximately 80° C./0.01 mm) or b) chromatography on a silica gel (pentane 100% then pentane/ethyl acetate 10/1) followed by filtration, water wash and drying, to yield 20.337 g (62%, not optimized) of a colorless solid. Analyses identical to the literature.

EXAMPLE 31

Synthesis of 4-(1,1,4-trimethyl-pentyl)bromobenzene[10] (WP133)

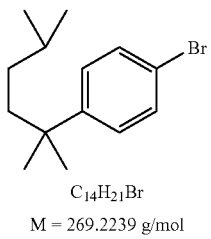

C$_{14}$H$_{21}$Br
M = 269.2239 g/mol

A 2 M solution of trimethylaluminum in hexane (10.5 ml, 2 eq) is slowly added to a solution of ketone WP132 prepared according to example 30 (2.675 g, 10.49 mmol) in chlorobenzene (4 ml) and water (100 µl) under a nitrogen atmosphere and cooled to 0° C. The hexane is then distilled and then the solution is heated at reflux for 80 hours. After cooling, the mixture is treated with the slow addition of water, then with 2 N HCl and is heated until the salts are dissolved. After cooling, the mixture is extracted several times with Et$_2$O. The recombined organic phases are washed successively with water then with a solution saturated with NaCl, dried on magnesium sulfate, filtered and concentrated under reduced pressure. The residue is then distilled (approximately 100° C./0.16 mm) to yield a mixture of products which is dissolved in 10 ml of dichloromethane, treated with 1.0 g of M-CPBA and stirred for 12 hours. After concentration under reduced pressure, the residue is purified by chromatography on a silica gel (pentane 100%) to yield 1.143 g (40%, not optimized) of a colorless liquid. Analyses identical to the literature.

EXAMPLE 32

Synthesis of Bis-Amidrazone (WP134)

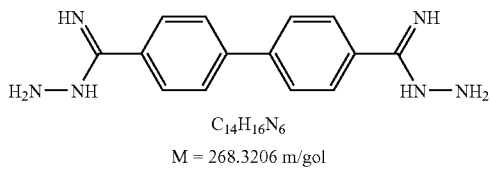

C$_{14}$H$_{16}$N$_6$
M = 268.3206 m/gol

Hydrazine monohydrate (637 µl, 13.1 mmol) is added over the course of 10 minutes to a suspension of WP129 prepared according to example 29 (1.296 g, 4.37 mmol) in absolute ethanol (7 ml). After 24 hours of stirring, the precipitate is filtered, washed successively with ethanol then with diethyl ether and is dried to yield 1.077 g (92%) of a yellow solid. δ$_H$ (300 MHz, DMSO) 5.00 (brs; 4H), 5.62 (s; 4H), 7.66 (d; J 8.7; 4H), 7.78 (d; J 8.7; 4H); MS (Electrospray) m/z 269 (MH$^+$, 100%).

EXAMPLE 33

Synthesis of 1,4-bis[5,6-(4,4'-diphenyl-1,2,4-triazine-3-yl]diphenyl (WP135)

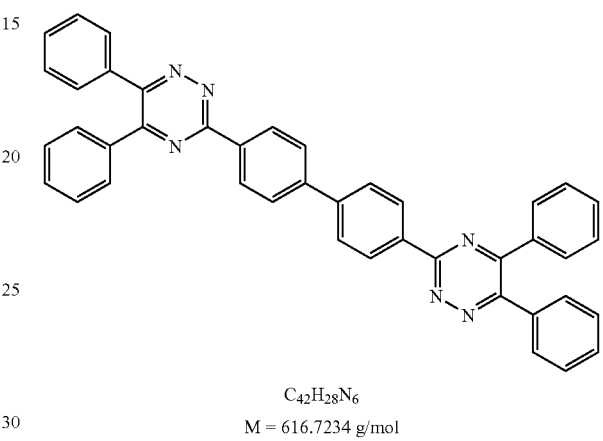

C$_{42}$H$_{28}$N$_6$
M = 616.7234 g/mol

WP134 prepared according to example 32 (300 mg, 1.12 mmol) is added all at once to a solution of benzyl (589 mg, 2.79 mmol) in ethanol (20 ml). The mixture is heated at reflux for 15 hours. After returning to ambient temperature, the precipitate obtained is filtered, washed successively with ethanol then with diethyl ether and is dried to yield 548 mg (80%) of a yellow solid. δ$_H$ (300 MHz, DMSO-d, 120° C.) 7.40-7.57 (m; 12H), 7.60 (m; 4H), 7.68 (m; 4H), 8.10 (d; 4H), 8.77 (d; 4H). MS (Electrospray) m/z 617 (MH$^+$, 10%), 457 (26%), 190 (100%).

EXAMPLE 34

Synthesis of 1,2-bis-[4(2-ethyl-hexyloxy)-phenyl]-ethane-1,2-dione (WP141)

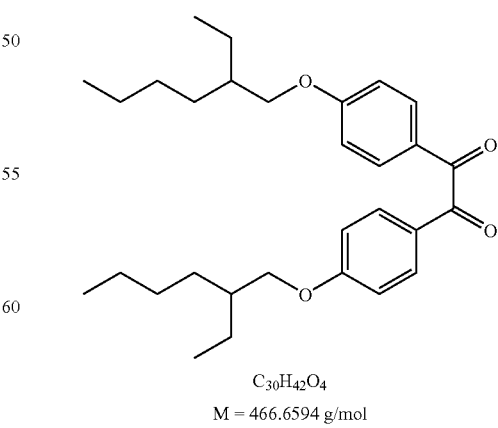

C$_{30}$H$_{42}$O$_4$
M = 466.6594 g/mol

Soda (1.24 g, 30.8 mmol) is added to a solution of WP32 prepared according to example 5 (3.00 g, 12.4 mmol) in DMF (75 ml). The mixture is stirred for 5 minutes at ambient temperature, then 2-ethylhexyl bromide (6.6 ml, 37.1 mmol) is added over the course of 1 minute. After 60 hours of stirring at 60° C., the mixture is cooled. The mixture is poured into iced water and extracted by ethyl acetate. The organic phase is washed several times with a solution saturated with sodium bicarbonate, dried on sodium sulfate, filtered and concentrated. The residue is purified by flash chromatography on a silica gel (pentane 100% then pentane/ethyl acetate 23/1) to yield 4.879 g (85%) of a yellow liquid. $\delta_H$ (300 MHz, CDCl$_3$) 0.90 (m; 12H), 1.25-1.35 (m; 8H), 1.45 (m; 8H), 1.75 (m; 2H), 3.91 (d; J 6.0; 4H), 6.94 (d; J 9.0; 4H), 7.92 (d; J 9.0; 4H); MS (Electrospray) m/z 954 (2M+H$^+$, 100%), 467 (MH$^+$, 33%).

EXAMPLE 35

Synthesis of 1,4-bis[5,6-bis(4,2-ethylhexyloxyphenyl)-1,2,4-triazine-3-yl]benzene (WP144)

EXAMPLE 36

Synthesis of 1,2-bis-[4-(1-methyl-heptyloxy)-phenyl]-ethane-1,2-dione (WP145)

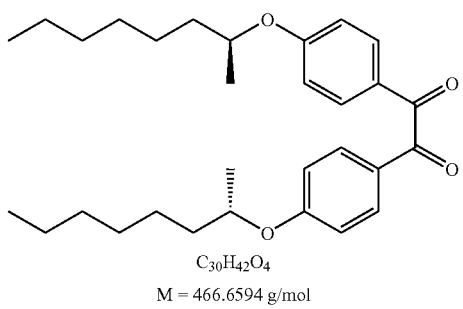

$C_{30}H_{42}O_4$
M = 466.6594 g/mol

Potassium carbonate (900 mg, 7.1 mmol) and then (S)-2-octyl tosylate[10] (740 mg, 2,6 mmol) are added to a solution

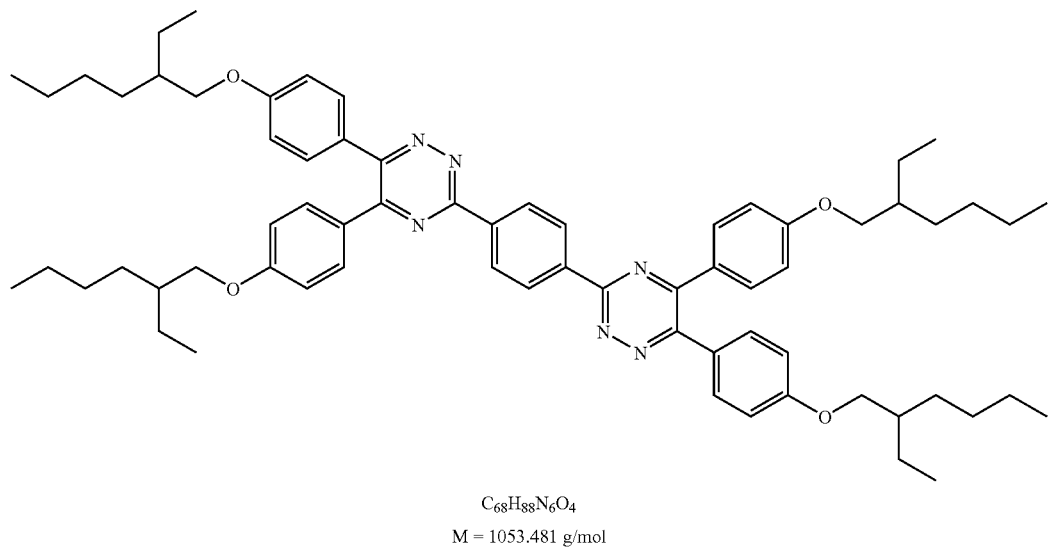

$C_{68}H_{88}N_6O_4$
M = 1053.481 g/mol

Terephthalamidrazone WP29 prepared according to example 3 (300 mg, 1.56 mmol) is added all at once to a solution of WP141 prepared according to example 34 (1.821 g, 1.52 mmol) in ethanol (40 ml). The mixture is heated at reflux for 15 hours. After returning to ambient temperature, the precipitate obtained is filtered, washed successively with ethanol then with diethyl ether and is dried to yield 1.452 g (88%) of a yellow solid. $\delta_H$ (300 MHz, CDCl$_3$) 0.90 (m; 24H), 1.25-1.60 (m; 32H), 1.74 (m; 4H), 3.89 (d; J 6.0; 8H), 6.92 (m; 8H), 7.63 (d; J 8.4; 4H), 7.74 (d; J 8.4; 4H), 8.82 (s; 4H); MS (Electrospray) m/z 1053 (MH$^+$, 100%).

of WP32 prepared according to example 5 (286 mg, 1.184 mmol) in DMF (6 ml). After 15 hours of stirring at 50° C., the mixture is cooled then poured into iced water and extracted by ethyl acetate. The organic phase is washed several times with a solution saturated with sodium bicarbonate, dried on sodium sulfate, filtered and concentrated. The residue is purified by flash chromatography on a silica gel (pentane 100% then pentane/ethyl acetate 20/1) to yield 406 mg (74%) of a yellow oil. $\delta_H$ (300 MHz, CDCl$_3$) 0.80-0.93 (m; 6H), 1.20-1.40 (m; 12H), 1.31 (d; J 6; 6H), 1.55 (m; 4H), 1.73 (m; 4H), 4.46 (m; 2H), 6.91 (d; J 9.3; 4H), 7.92 (d; J 9.3; 4H); MS (Electrospray) m/z 955 (2M+Na$^+$, 100%), 467 (MH$^+$, 56%).

EXAMPLE 37

Synthesis of 1,4-bis[5,6-bis(4,1-methylheptyloxyphenyl)-1,2,4-triazine-3-yl]benzene (WP149)

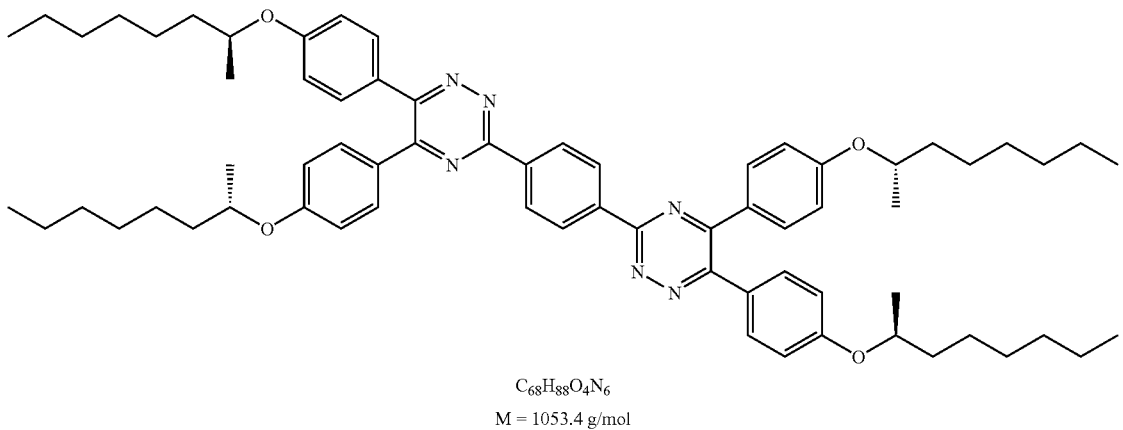

$C_{68}H_{88}O_4N_6$
M = 1053.4 g/mol

Terephthalamidrazone WP29 prepared according to example 3 (69 mg, 0.355 mmol) is added all at once to a solution of WP145 prepared according to example 36 (398 mg, 0.85 mmol) in ethanol (8 ml). The mixture is heated at reflux for 15 hours. After returning to ambient temperature, the precipitate obtained is filtered, washed successively with ethanol then with cold pentane and dried to yield a yellow solid (yield not calculated). $\delta_H$ (300 MHz, CDCl$_3$) 0.80-0.95 (m; 12H), 1.20-1.53 (m; 24H), 1.31 (d; J 6; 12H), 1.60 (m; 8H), 1.75 (m; 8H), 4.42 (m; 4H), 6.88 (d; J 9.0; 4H), 6.91 (d; J 9.0; 4H), 7.63 (d; J 9.0; 4H), 7.73 (d; J 9.0; 4H), 8.82 (s; 4H); MS (Electrospray) m/z 1053 (MH$^+$, 100%).

EXAMPLE 38

Synthesis of 1,2-bis-[4-(1,1,4-trimethyl-pentyl)-phenyl]-ethane-1,2-dione (WP150)

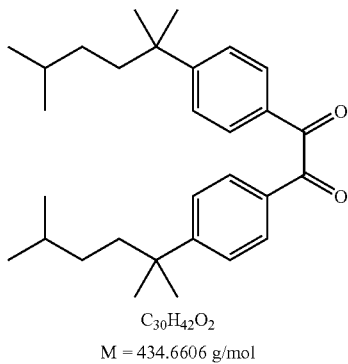

$C_{30}H_{42}O_2$
M = 434.6606 g/mol

A solution of s-BuLi (1.3 M in cyclohexane, 2.9 ml, 3.71 mmol) is added slowly to a solution of WP133 prepared according to example 31 (1.0 g, 3.71 mmol) in anhydrous THF (4.6 ml) at −78° C. and under a nitrogen atmosphere. After 1 hour of stirring during which 3 additional ml of THF are added, the mixture is heated to approximately 0° C. then transferred using a cannula to a suspension of 1,4-dimethylpiperazine-2,3-dione (240 mg, 1.688 mmol) in THF (6 ml) cooled to 0° C. After returning to ambient temperature, the mixture is stirred for 3 hours then treated with 2 N HCl. After dilution with Et$_2$O, the organic phase is separated and the aqueous phase is extracted twice with Et$_2$O. The recombined organic phases are washed with water and then with a solution saturated with NaCl and are dried on magnesium sulfate. After filtration and concentration, the residue is purified by flash chromatography on a silica gel (pentane/ethyl acetate 100/0; 6/1; 4/1) to yield 523 mg (71%, not optimized) of a yellow oil. $\delta_H$ (300 MHz, CDCl$_3$) 0.80 (d; J 6.0; 12H), 0.85-0.97 (m; 4H), 1.3 (s; 12H), 1.40 (sept.; J 6.0; 2H), 1.55-1.70 (m; 4H), 7.45 (d; J 8.7; 4H), 7.91 (d; J 8.7; 4H).

EXAMPLE 39

Synthesis of bis(4-(1,1,4-trimethylpentyl)phenyl)-1,2,4-triazine-3-yl]benzene (WP151)

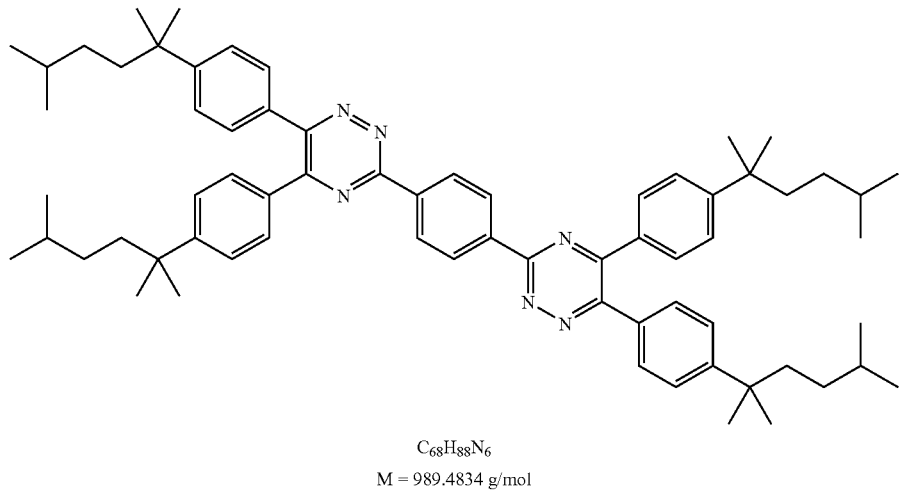

$C_{68}H_{88}N_6$
M = 989.4834 g/mol

Terephthalamidrazone (104 mg, 0.544 mmol) is added all at once to a solution of WP150 prepared according to example 38 (520 mg, 1.196 mmol) in ethanol (10 ml). The mixture is heated at reflux for 15 hours. After returning to ambient temperature, the precipitate obtained is filtered, washed with ethanol and dried to yield 348 mg (65%, not optimized) of a yellow solid. $\delta_H$ (300 MHz, CDCl$_3$) 0.81 (d; J 6.0; 24H), 0.90-0.10 (m; 8H), 1.31 (s; 24H), 1.40 (sept.; J 6.0; 4H), 1.53-1.70 (m; 8H), 7.33 (d; J 8.7; 4H), 7.34 (d; J 8.7; 4H), 7.58 (d; J 8.7; 4H), 7.66 (d; J 8.7; 4H); MS (Electrospray) m/z 1978 (2M+H+, 30%), 989 (MH+, 100%).

BIBLIOGRAPHICAL REFERENCES FOR SYNTHESES (1) G. Pitet, H. Cousse, G. Mouzin, *Boll. Chim. Farm.*, 1980, 119, 469
(2) F. Lu, Y. Wang, L. Xing, *Gaofenzi Tongxun*, 1981, 5, 319
(3) X. Yi, G. Wu, F. Lu, A. Tang, *J. Appl. Polym. Sci.*, 2001, 907, 82
(4) H. Simbürger, W. Kern, K. Hummel, C. Hagg, *Polym.*, 2000, 41, 7883
(5) L. Brunsvelt, H. Zhang, M. Glasbeek, A. J. M. Vekemans, E. W. Meijer, *J. Am. Chem. Soc.*, 2000, 122, 6175
(6) T. Tagusari, Y. Honda, *Jpn. Kokai Tokkyo Koho*, 1992, JP 04279546
(7) M. Wehmeier, M. Wagner, K. Mullen, *Chem. Eur. J.*, 2001, 7, 2197
(8) T. Shono, M. Masahiro, S. Matsumura, N. Asano, *Jpn. Tokkyo Koho*, 1968, JP 43015992
(9) U.S. Pat. No. 5,202,471, 1993
(10) M. S. Alnajjar, H. G. Kuivila, *J. Am. Chem. Soc.*, 1985, 107, 422.

Below are found the physicochemical studies carried out on the compounds which are objects of the present invention, in comparison with the following commercial filters:

PARSOL 1789®:

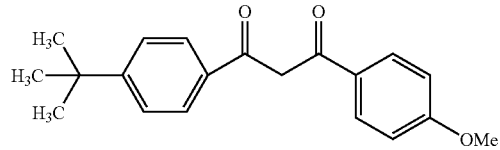

PARSOL MCX®:

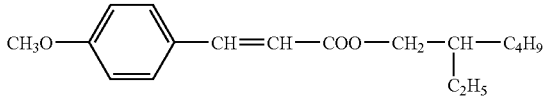

TINOSORBS®:

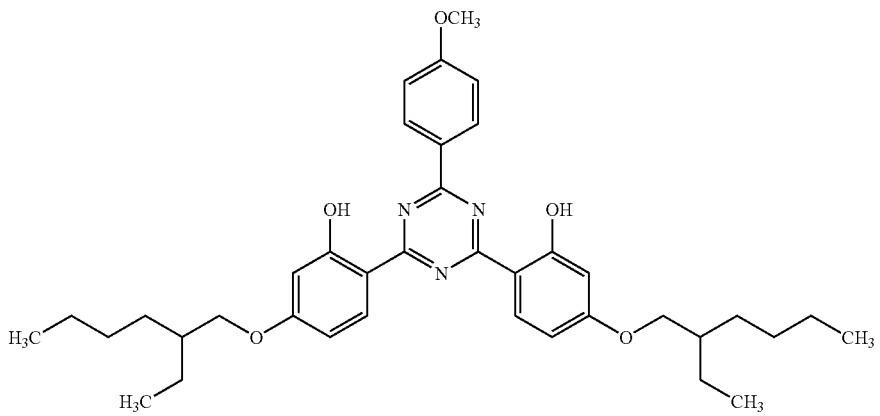

TINOSORB M®:

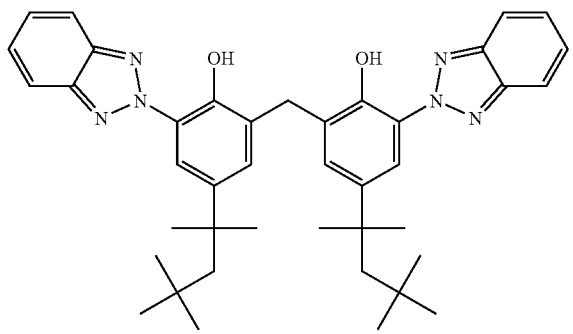

EXAMPLE 40

Spectral Characteristics of the Products

Molar Extinction Coefficient and Specific Absorbance

The calculation of the molar extinction coefficient ($\epsilon$) is made from the Beer-Lambert law:

$$\mathrm{Log}_{10}\left(\frac{I_0}{I}\right) = \varepsilon \cdot l \cdot c = A$$

Wherein:
A=absorbance
$I_0$=intensity of the incident light
I=intensity of the transmitted light
$\epsilon$=molar extinction (or molar absorbance) coefficient in $M^{-1}$ $cm^{-1}$
l=path length in cm
c=concentration in mol/l The molar extinction coefficient can be expressed with respect to a given mass of the product. It thus makes it possible to be able to compare the coefficients of extinction between products for the same given quantity. This quantity is 1% by weight. The molar extinction coefficient thus becomes the specific absorbance ($A_{1cm}^{1\%}$).

It is expressed as follows:

$$A_{1\,cm}^{1\%} = \varepsilon \cdot \frac{10}{M}$$

Wherein:
$A_{1cm}^{1\%}$=specific absorbance
$\epsilon$=molar extinction coefficient
M=molar mass The spectral characteristics of the compounds in comparison with commercial filters at a concentration of 10 µg/ml are summarized in tables 2-1 and 2-2.

Procedure: The products are dissolved in ethyl acetate to a concentration of 10 µg/ml. The spectra are measured using a dual-beam spectrophotometer (Varian CARY 50 Scan) between 290 nm and 400 nm.

TABLE 2-1

| Molecules | Maximum molar extinction coefficient | | | | Maximum specific absorbance | | | |
|---|---|---|---|---|---|---|---|---|
| | UVC | UVB | UVA | Visible | UVC | UVB | UVA | Visible |
| PARSOL 1789 ® | 8633 at 275 | | 34100 at 360 | | 278 at 275 | | 1100 at 360 | |
| PARSOL MCX ® | | 24600 at 310 | | | | 848 at 310 | | |
| TINOSORB S ® | | 41750 at 310 | 49580 at 345 | | | 751 at 310 | 789 at 345 | |
| TINOSORB M ® | | 36600 at 305 | 36400 at 345 | | | 556 at 305 | 552 at 345 | |

TABLE 2-2

| | Compounds of formula (I) | | | | | | | |
|---|---|---|---|---|---|---|---|---|
| | Maximum molar extinction coefficient | | | | Maximum specific absorbance | | | |
| Molecules | UVC | UVB | UVA | Visible | UVC | UVB | UVA | Visible |
| WP30 | | | 50200 at 325 | | | | 928 at 325 | |
| WP35 | | 29600 at 310 | 27800 at 355 | | | 490 at 310 | 460 at 355 | |
| WP39 | | | 48200 at 335 | | | | 808 at 335 | |
| WP41 | | 72000 at 305 | 91400 at 330 | | | 527 at 305 | 669 at 330 | |
| WP52 | | | 57300 at 330 | | | | 669 at 330 | |
| WP76 | | 54000 at 290 | | | | 998 at 290 | | |
| WP89 | | | 47700 at 330 | | | | 778 at 330 | |
| WP96 | | | 56000 at 335 | | | | 638 at 335 | |
| WP100 | | | 43400 at 300 | | | | 640 at 100 | |
| WP104 | | 90000 at 300 | | | | 1176 at 300 | | |
| WP107 | | 92000 at 300 | 95000 at 335 | | | 757 at 300 | 783 at 335 | |
| WP135 | | | 57000 at 330 | | | | 924 at 330 | |
| WP144 | | 66000 at 315 | 64000 at 355 | | | 626 at 315 | 607 at 355 | |
| WP149 | | 56000 at 315 | 59000 at 355 | | | 532 at 315 | 560 at 355 | |
| WP151 | | | 60500 at 340 | | | | 611 at 340 | |

EXAMPLE 41

The products tested are classified according to spectral distribution in UVA and UVB in a range from 290 nm to 400 nm. It is possible to differentiate them according to their spectral distribution:

Products with a narrow spectrum:
Products absorbing in the range between 280 nm and 320 nm (UVB)
Products absorbing in the range between 320 nm and 400 nm (UVA)
Products with a broad spectrum:
Products absorbing in UVB (280-320 nm) and UVA-II (380-360 nm)
Products covering UVB and UVA (280-400 nm).

EXAMPLE 41-1

Spectral Distribution of Compounds of Formula (I)

Figure 2:
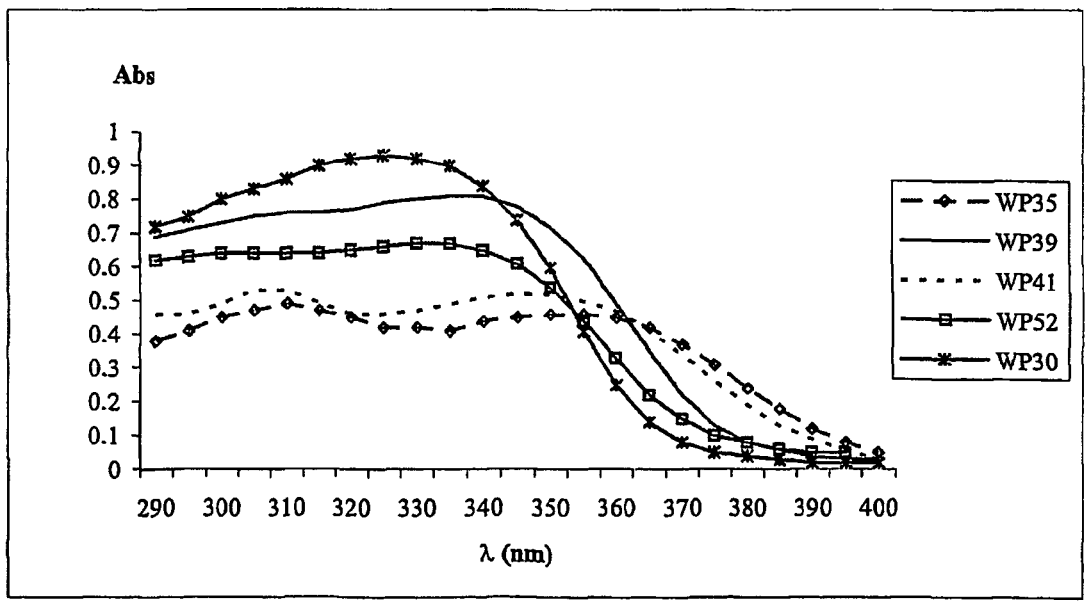
FIG. 2 represents the UV-A and UV-B absorption spectra of compounds WP35, WP39, WP41, WP52 and WP30.

WP89, WP96, WP100, WP104, WP107, WP135, WP144, WP149, WP151, WP35, WP39, WP41, WP52 and WP30 absorb in UVB and UVA (see FIGS. 1 and 2).

Figure 3:
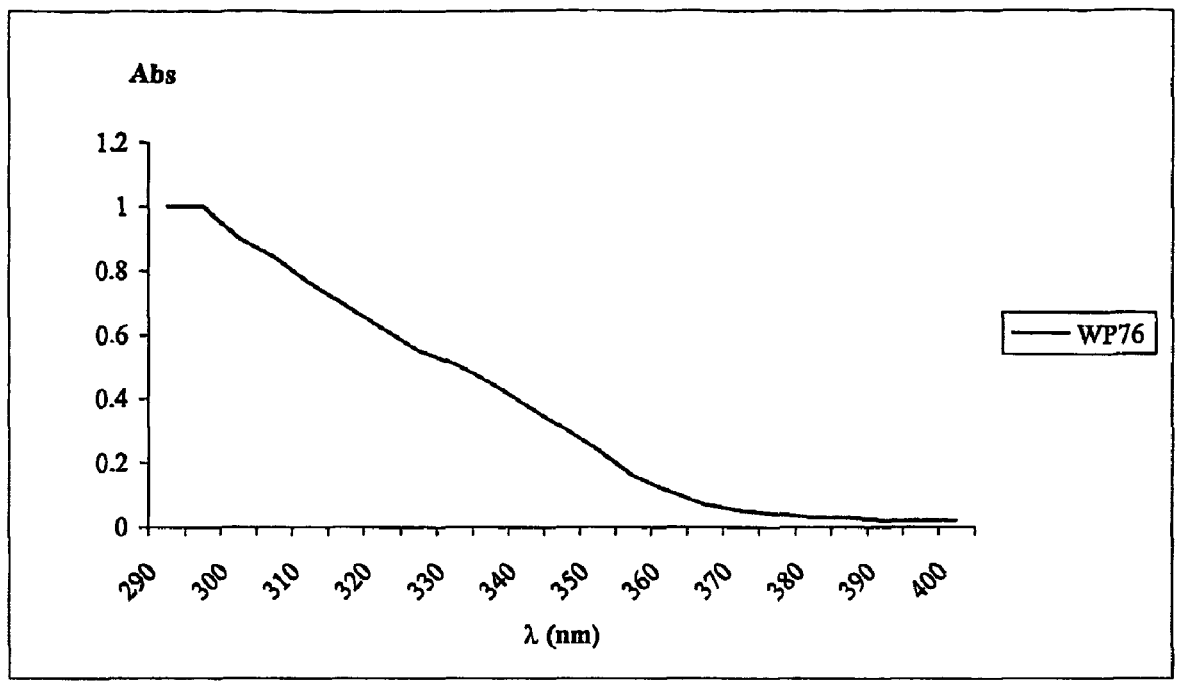
FIG. 3 represents the UV-A and UV-B absorption spectra of compound WP76.

WP76 absorbs in UVB (see FIG. 3).

EXAMPLE 41-2

Table 3 summarizes the spectral distributions of the compounds tested.

TABLE 3

| Molecules | UVB 280-320 nm | UVA-II 320-340 nm | UVA-I 340-400 nm | Absorption peaks(nm) |
|---|---|---|---|---|
| Parsol 1789 ® | | Average | | 360 |
| WP76 | | Strong | | 290 |
| Parsol ® | | | | 310 |
| Tinosorb S ® | | | | 310 and 345 |
| Tinosorb M ® | | | | 305 and 345 |
| WP30 | | | | 325 |
| WP35 | | | Average | 355 |
| WP39 | | | Average | 335 |
| WP41 | | | | 205 and 330 |
| WP52 | | | Strong | 330 |
| WP89 | | | Average | 330 |
| WP96 | | | Average | 335 |
| WP100 | | Strong | Strong | 300 |
| WP104 | | Strong | Average | 300 |
| WP107 | | | Average | 300 and 335 |
| WP135 | | | Average | 330 |
| WP144 | | | | 315 and 355 |
| WP149 | | | | 315 and 355 |
| WP151 | | | Average | 340 |

Legend:
- Very strong absorption
- ▨ Strong absorption
- ■ Average absorption
- ▨ Weak absorptoin
- No absorption

EXAMPLE 42

Evaluation of Sun Protection Factor (SPF) In Vitro in a Chemical Solvent

The in vitro methods of determining the protective effectiveness of sun products consist of measuring by transmission spectrophotometry the absorption spectrum of the filter in solution or of the product applied on a substrate with the aim of simulating the surface of the skin. The effectiveness against UVB and/or UVA rays, or the effect on the cutaneous response, are then determined by calculation, taking into account or not the UV radiation action spectrum for the damage considered.

The Sayre/Agin and Diffey/Robson method, used since the 1990s, involves a comparative measurement, with the aid of an integrating-sphere spectroradiometer, of the transition from 290 nm to 400 nm in 5 nm steps, the sample being subjected to UV radiation from a stable known source covering the whole of the UV spectrum (unfiltered xenon).

Diffey and Robson evaluate the erythemal response by the following calculation:

$$FPS = \frac{\left(\sum_{290}^{400} E(\lambda) * \varepsilon\right)}{\left(\sum_{290}^{400} \frac{E(\lambda) * \varepsilon}{FPM(\lambda)}\right)}$$

$E(\lambda)$=spectral irradiation in $W(m^{-2})$ $(nm^{-1})$ at 40° N sun at 20° zenith angle $\epsilon$=erythematous capacity $$\overline{FPM}(\lambda) = \frac{\left(\sum_{i=1}^{N} FPM(\lambda)i\right)}{N(\lambda)}$$

$N(\lambda)$=number of values for a given wavelength

The Diffey and Robson formula makes it possible to determine SPF from the measurement of transmittance between 290 nm and 400 nm. Transmittance is measured in solution in ethyl acetate at a concentration of 10 µg/ml using a UV-visible spectrophotometer (Varian CARY 50 Scan).

$$FPM(\lambda) = \frac{1}{T(\lambda)}$$

$T(\lambda)$=transmittance at wavelength $\lambda$

The results of the measurements taken are summarized in table 5.

TABLE 4

| In vitro SPF measurement in a chemical solvent | |
|---|---|
| Molecules | SPF |
| Parsol MCX ® | 20.78 |
| Parsol 1789 ® | 51.1 |
| Tinosorb M ® | 54.07 |
| Tinosorb S ® | 76.19 |
| Compounds of formula (I) | |
| WP96 | 68.02 |
| WP104 | 79.35 |
| WP149 | 74.1 |
| WP151 | 67.2 |

EXAMPLE 43

Study of Photostability in Solution in a Chemical Solvent

A Suntest CPS+(Atlas, Linsengenicht/Altenhasslan, Germany) was used. The Suntest makes it possible to reproduce the solar spectrum and thus to carry out exposures inside at any time without weather constraints.

Setting the MED (Minimal Erythemal Dose):

The radiance of the solar simulator was carefully measured with a spectroradiometer (MSS 2044, Bielefeld, Germany). UVB and UVA intensities were 0.49 $mW/cm^2$ and 6.32 $mW/cm^2$, respectively. The MED value defined by COLIPA is 5.6 $J/cm^2$ in total UV (22). The UV total (UVA+UVB) accounts for 14.8% of the energy delivered by the lamp (power 460 $W/m^2$). An irradiation dose equivalent to 1 MED corresponds to 37.83 $J/cm^2$ (in total spectrum) delivered by the lamp.

The Suntest test duration is calculated using the following formula:

$t=H/E$ with:
E=illumination energy in $W/m^2$
H=irradiation dose in $J/m^2$
t=duration of the test in s The setting of the MED on the Suntest and the correspondence with sun intensity at 3 seaside resorts are indicated in table 6.

TABLE 6

| | Sun intensity | | |
|---|---|---|---|
| | Extreme | Intense | Average |
| Location (June 21) | Agadir | Toulon | La Baule |
| Number of MED/d | 20 | 10 | 5 |
| Dose of corresponding irradiation on the Suntest (in $J/m^2$) | 7566000 | 3783000 | 1891500 |
| Test duration | 4 h 34 min | 2 h 17 min | 1 h 8 min |

Procedure:

The solutions of the compounds are prepared at a concentration of 500 µg/ml in methanol. 50 µl (25 µg) of each solution are deposited in a crystallizer, then irradiated in the Suntest at 5, 10 and/or 20 MED. A non-irradiated control is prepared (deposit of 50 µl of solution and addition of 2.450 ml of methanol). The solvent evaporates during irradiation and the products are taken up in 2.5 ml of methanol. After irradiation, the absorbance of each solution is measured with the UV-visible spectrophotometer (Varian CARY 50 Scan).

The photostability measurement results for the compounds of formula (I) are summarized in table 7.

TABLE 7

| | Photostability at 5 MED | | | Photostability at 10 MED | | |
|---|---|---|---|---|---|---|
| molecule | mean | standard deviation | relative standard deviation | mean | standard deviation | relative standard deviation |
| WP30 | 77.75 | 0.78 | 1.00% | 56.12 | 0.54 | 137.83% |
| WP76 | 69.23 | 1.31 | 1.89% | 62.53 | 0.91 | 137.39% |
| WP96 | 83.30 | 5.94 | 7.13% | 74.35 | 4.15 | 138.07% |
| WP104 | 93.70 | 4.24 | 4.53% | 88.55 | 2.97 | 138.43% |
| WP107 | 89.27 | 1.46 | 1.64% | 84.75 | 1.02 | 138.29% |
| WP135 | 57.45 | 1.63 | 2.83% | 33.66 | 1.13 | 136.58% |
| WP149 | 80.40 | 1.56 | 1.93% | 38.16 | 1.09 | 137.95% |
| WP151 | 76.16 | 4.30 | 5.64% | 70.15 | 3.00 | 137.76% |

EXAMPLE 44

Solubility Study

The solubility results for solvents or excipients used in cosmetics are summarized in table 8.

TABLE 8

| Compounds of formula (I) | | |
|---|---|---|
| Molecules | Excipients | Solubility (%) |
| WP96 | Myritol 318 ® | 0.1 |
| | Finsol V NT ® | 1 |
| | PEG400 ® | 2 |
| WP107 | Finsol V NT ® | 1 |
| | PEG400 ® | 1 |
| | Arlasolve DMI ® | 1 |

TABLE 8-continued

| Compounds of formula (I) | | |
|---|---|---|
| Molecules | Excipients | Solubility (%) |
| WP149 | Myritol 318 ® | 2.5 |
| | Finsol V NT ® | 4.5 |
| | Isopropyl adipate | 2 |
| WP151 | Myritol 331 ® | 2 |
| | Finsol V NT ® | 5 |
| | Isopropyl adipate | 1 |
| | PEG400 ® | 0.5 |

Arlasolve DMI ® = dimethyl isosorbide
Finsol V NT ® = $C_{12}$-$C_{15}$ alkyl benzoate
Myritol 318 ® = caprylic/capric triglycerides
Myritol 331 ® = cocoglycerides (glyceryl esters and derivatives)
PEG400 ® = polyethylene glycol (n = 400)

TABLE 9

| Compounds of formula (I) | | |
|---|---|---|
| | Solubilities | |
| Molecules | Soluble | Insoluble |
| WP30 | DMSO or hot DMF | Water |
| | Ethyl acetate (PS) | MeOH |
| | | CHCl$_3$ |
| | | Acetone |
| | | Acetonitrile |
| | | Benzene |
| | | Myritol |
| | | Transcutol |
| WP35 | DMSO 3.5% | MeOH |
| | Transcutol 0.5% | CHCl$_3$ |
| | | Ethyl acetate |
| | | Hexane |
| | | Myritol |
| WP38 | Benzene | MeOH |
| | Toluene | DMC |
| | Myritol | AcOEt |
| | Transcutol | |
| WP39 | DMSO or hot DMF | Water |
| | | MeOH |
| | | CHCl$_3$ |
| | | Acetone |
| | | Acetonitrile |
| | | Benzene |
| WP40 | DMSO or hot DMF | Water |
| | | MeOH |
| | | CHCl$_3$ |
| | | Acetone |
| | | Acetonitrile |
| | | Benzene |
| WP41 | DMC | EtOH |
| | AcOEt (PS) | Hexane |
| | MeOH (PS) | Myritol |
| | DMSO 2.7% | |
| | Transcutol 0.1% | |
| WP52 | DMSO or hot DMF | Water |
| | | MeOH |
| | | CHCl$_3$ |
| | | Acetone |
| | | Acetonitrile |
| | | Benzene |
| | | Myritol |
| | | Transcutol |
| WP76 | DMSO or hot DMF | Water |
| | | MeOH |
| | | CHCl$_3$ |
| | | Acetone |
| | | Acetonitrile |
| | | Benzene |

TABLE 9-continued

| Compounds of formula (I) | | |
|---|---|---|
| | Solubilities | |
| Molecules | Soluble | Insoluble |
| WP89 | Ethyl acetate | |
| WP96 | DMC | EtOH |
| | CHCl$_3$ | Myritol |
| | Et$_2$O | Acetic acid |
| | Toluene | |
| | Octanol | |
| | Transcutol 0.5% | |
| | Methanol | |
| WP100 | Hot DMSO | DCM |
| | | Et$_2$O |
| | | Toluene |
| | | Octanol |
| | | EtOH |
| | | Myritol |
| | | Transcutol |
| WP104 | DCM | EtOH |
| | CHCl$_3$ | MeOH |
| | Toluene | 1-Octanol |
| | DMSO | Acetic acid |
| | Ethyl acetate | Myritol Transcutol |
| WP107 | DCM | EtOH |
| | CHCl$_3$ | Acetic acid |
| | Toluene | MeOH |
| | Octanol | Myritol |
| | Ethyl acetate | Transcutol |
| | DMSO | |

DMSO: dimethylsulfoxide
DMF: dimethylformamide
DCM: dichloromethane

EXAMPLE 45

Formulation Example

| Composition (H/E emulsion) | Quantity (g) |
|---|---|
| Hydrated magnesium sulfate | 0.7 |
| Ethyl hexyl para methoxy cinnamate | 5 |
| WP151 | 5 |
| C$_{12}$-C$_{15}$ alcohol benzoate | 10 |
| Titanium oxide | 3 |
| Triethanolamine | Qs pH 7 |
| Glyceride | 3 |
| Preservatives | Qs |
| Demineralized water | qsp 100 |

The invention claimed is:

1. 5,6-diphenyl-1,2,4-triazinic compound of general formula (I):

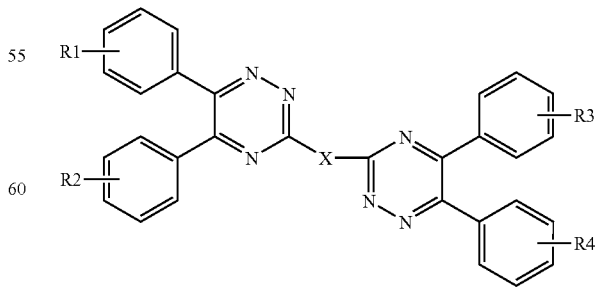

(I)

wherein:
R$_1$, R$_2$, R$_3$ and R$_4$, identical or different, represent a hydrogen, fluorine, chlorine or bromine atom, a C$_1$ to C$_{12}$ linear or branched alkyl group, a hydroxy group, a $C_1$ to $C_{18}$ linear or branched alkoxy group, a poly(ethoxy)-alkoxy group with a $C_1$ to $C_4$ alkyl fragment and an ethoxy number ranging from 1 to 4, an amino group, or a mono- or di-alkylamino group with a $C_1$ to $C_4$ alkyl fragment, X represents an ortho-, meta- or para-phenylene group, a 4,4'-biphenylene group, a 2,4- or 2,6- or 3,4- or 3,5-pyridinylene group, a 2,2'-bipyridinylene group, a meta- or para-phenylenediamino group, an ethylenediamino group, a 2,2'-piperazinylene group, a diacyl group of formula —$(R_4CO)_2$— wherein $R_4$ represents a phenyl radical, an alkylated chain of 3 to 10 carbon atoms, a phenanthrenylene group or an anthracenylene group, with the exception of 1,4-bis(5,6-diphenyl-1,2,4-triazin-3-yl)benzene, 2,4-bis(5,6-diphenyl-1,2,4-triazin-3-yl)pyridine, and 2,6-bis(5,6-diphenyl-1,2,4-triazin-3-yl)pyridine.

2. 5,6-diphenyl-1,2,4-triazinic compound of formula (I) according to claim 1, wherein:

$R_1$, $R_2$, $R_3$ and $R_4$ represent a $C_1$ to $C_{12}$ linear or branched alkyl group located in the para position, or a $C_1$ to $C_{18}$ linear or branched alkoxy group located in the para position, and X represents a 4,4'-biphenylene group.

3. 5,6-diphenyl-1,2,4-triazinic compound according to claim 1, selected from the group consisting of:

WP35: 1,4-Bis[5,6-(4,4'-dihydroxy)-diphenyl-1,2,4-triazin-3-yl]benzene

WP38: 1,4-Bis[5,6-(4,4'-di-octadecyloxy)-diphenyl-1,2,4-triazin-3-yl]benzene

WP39: 1,4-Bis[5,6-(4,4'-dimethyl)-diphenyl-1,2,4-triazin-3-yl]benzene

WP40: 1,4-Bis[5,6-(4,4'-dimethoxy)-diphenyl-1,2,4-triazin-3-yl]benzene

WP41: 1,4-Bis[5,6-(4,4'-(2-{2-[2-(2-methoxy-ethoxy)-ethoxy]-ethoxy}-ethoxy)-) -diphenyl-1,2,4-triazin-3-yl]benzene WP52: 1,4-Bis-[5,6-(4,4'-dibromo)-diphenyl-1,2,4-triazin-3-yl]benzene WP76: 1,3-Bis(5,6-diphenyl-1,2,4-triazin-3-yl)benzene WP89: 1,4-Bis[5,6-(4,4'-difluoro)-diphenyl-1,2,4-triazin-3-yl]benzene WP96: 1,4-Bis[5,6-(4,4'-dihexyl)-diphenyl-1,2,4-triazin-3-yl]benzene WP100: 1,4-Bis[5,6-(4,4'-dichloro)-diphenyl-1,2,4-triazin-3-yl]benzene WP104: 1,4-Bis[5,6-(4,4'-4-di-tert-butyl)-diphenyl-1,2,4-triazin-3-yl]benzene WP107: 1,4-Bis[5,6-bis(4-dodecylphenyl)-1,2,4-triazine-3-yl]benzene WP135: 1,4-bis-[5,6-(4,4'-diphenyl-1,2,4-triazine-3-yl] diphenyl WP144: 1,4-bis-[5,6-bis(4,2-ethylhexyloxyphenyl)-1,2,4-triazine-3-yl]benzene WP149: 1,4-bis[5,6-bis(4,1-methylheptyloxyphenyl)-1,2,4-triazine-3-yl]benzene WP151: bis(4-(1,1,4-trimethylpentyl)phenyl)-1,2,4-triazine-3-yl]benzene.

4. A cosmetic sunscreen composition active in UV-A and/or UV-B and/or UV-C containing an effective quantity of one or more 5,6-diphenyl-1,2,4-triazinic compound of formula (I):

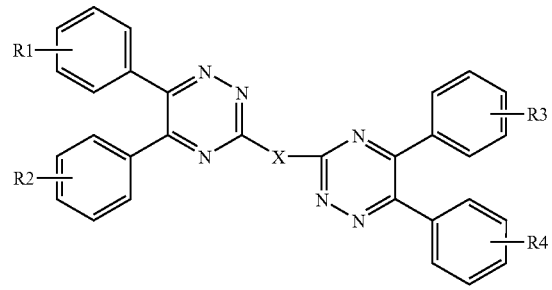

wherein:

$R_1$, $R_2$, $R_3$ and $R_4$, identical or different, represent a hydrogen, fluorine, chlorine or bromine atom, a $C_1$ to $C_{12}$ linear or branched alkyl group, a hydroxy group, a $C_1$ to $C_{18}$ linear or branched alkoxy group, a poly(ethoxy)-alkoxy group with a $C_1$ to $C_4$ alkyl fragment and an ethoxy number ranging from 1 to 4, an amino group, or a mono- or di-alkylamino group with a $C_1$ to $C_4$ alkyl fragment, X represents an ortho-, meta- or para-phenylene group, a 4,4'-biphenylene group, a 2,4- or 2,6- or 3,4- or 3,5-pyridinylene group, a 2,2'-bipyridinylene group, a meta- or para-phenylenediamino group, an ethylenediamino group, a 2,2'-piperazinylene group, a diacyl group of formula —$(R_4CO)_2$— wherein $R_4$ represents a phenyl radical, an alkylated chain of 3 to 10 carbon atoms, a phenanthrenylene group or an anthracenylene group in combination with a cosmetically acceptable excipient.

5. A cosmetic sunscreen composition according to claim 4, wherein containing in addition one or more sun filters active in UV-A and/or UV-B and/or UV-C.

6. A sun filter active in UV-A and/or UV-B and/or UV-C for human skin and/or hair, containing one or more 5,6-diphenyl-1,2,4-triazinic compound of general formula (I):

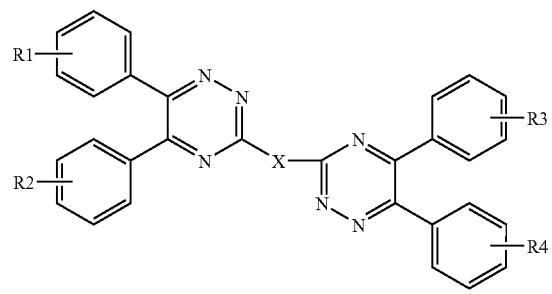

wherein:

$R_1$, $R_2$, $R_3$ and $R_4$, identical or different, represent a hydrogen, fluorine, chlorine or bromine atom, a $C_1$ to $C_{12}$ linear or branched alkyl group, a hydroxy group, a $C_1$ to $C_{18}$ linear or branched alkoxy group, a poly(ethoxy)-alkoxy group with a $C_1$ to $C_4$ alkyl fragment and an ethoxy number ranging from 1 to 4, an amino group, or a mono- or di-alkylamino group with a $C_1$ to $C_4$ alkyl fragment, X represents an ortho-, meta- or para-phenylene group, a 4,4'-biphenylene group, a 2,4- or 2,6- or 3,4- or 3,5-pyridinylene group, a 2,2'-bipyridinylene group, a meta- or para-phenylenediamino group, an ethylenediamino group, a 2,2'-piperazinylene group, a diacyl group of formula —$(R_4CO)_2$— wherein $R_4$ represents a phenyl radical, an alkylated chain of 3 to 10 carbon atoms, a phenanthrenylene group or an anthracenylene group.

7. A light-protective agent active in UV-A and/or UV-B and/or UV-C, useful in the synthetic materials industry, containing one or more 5,6-diphenyl-1,2,4-triazinic compound of formula (I) as defined in claim 6.

8. The light-protective agent according to claim 7 as light-protective agents incorporated into the composition of plastics, glass or textiles.

9. A cosmetic sunscreen composition according to claim 4, wherein the effective quantity of the one or more 5,6-diphenyl-1, 2, 4-triazinic compound of formula (I) is comprised of between 0.1% and 20% by weight with respect to the total weight of the composition.

10. A cosmetic sunscreen composition according to claim 4, wherein the one or more 5,6-diphenyl-1,2,4-triazinic compound of formula (I) comprises 1,4-bis(5,6-diphenyl-1,2,4-triazin-3-yl) benzene.

11. A sun filter according to claim 6, wherein the one or more 5,6-diphenyl-1,2,4-triazinic compound of formula (I) comprises 1,4-bis(5,6-diphenyl-1,2,4-triazin-3-yl)benzene.

12. A light-protective agent according to claim 7, wherein the one or more 5,6-diphenyl -1,2,4-triazinic compound of formula (I) comprises 1,4-bis (5,6-diphenyl-1,2,4-triazin-3-yl)benzene.

\* \* \* \* \*